United States Patent
Cohen et al.

(10) Patent No.: US 11,129,837 B2
(45) Date of Patent: Sep. 28, 2021

(54) SALICYLATE COMPOUND COMPOSITION

(71) Applicant: Innovate Pharmaceuticals Limited, Prestwich (GB)

(72) Inventors: Simon Jason Cohen, Manchester (GB); Craig Hurst, Stoke-On-Trent (GB)

(73) Assignee: INNOVATE PHARMACEUTICALS LIMITED, Manchester (GB)

( * ) Notice: Subject to any disclaimer, the term of this patent is extended or adjusted under 35 U.S.C. 154(b) by 403 days.

(21) Appl. No.: 15/538,974

(22) PCT Filed: Dec. 22, 2015

(86) PCT No.: PCT/GB2015/054129
§ 371 (c)(1),
(2) Date: Jun. 22, 2017

(87) PCT Pub. No.: WO2016/102959
PCT Pub. Date: Jun. 30, 2016

(65) Prior Publication Data
US 2017/0348332 A1  Dec. 7, 2017

(30) Foreign Application Priority Data

Dec. 23, 2014  (GB) .................................... 1423109
Aug. 7, 2015   (GB) .................................... 1514012

(51) Int. Cl.
| | | |
|---|---|---|
| A61K 31/616 | (2006.01) | |
| A61K 47/14  | (2017.01) | |
| A61K 9/08   | (2006.01) | |
| A61K 9/00   | (2006.01) | |
| A61K 47/20  | (2006.01) | |
| A61K 47/22  | (2006.01) | |
| A61K 47/44  | (2017.01) | |

(52) U.S. Cl.
CPC .......... *A61K 31/616* (2013.01); *A61K 9/0053* (2013.01); *A61K 9/0056* (2013.01); *A61K 9/0095* (2013.01); *A61K 9/08* (2013.01); *A61K 47/14* (2013.01); *A61K 47/20* (2013.01); *A61K 47/22* (2013.01); *A61K 47/44* (2013.01)

(58) Field of Classification Search
CPC ...... A61K 31/616; A61K 47/14; A61K 47/20; A61K 47/22; A61K 47/44; A61K 9/0053; A61K 9/0056; A61K 9/0095; A61K 9/08
USPC ......................................................... 514/165
See application file for complete search history.

(56) References Cited

U.S. PATENT DOCUMENTS

| | | | |
|---|---|---|---|
| 3,316,150 A | | 4/1967 | Faeges et al. |
| 4,375,468 A | * | 3/1983 | Dunn .................. A61K 9/2013 424/468 |
| 5,110,606 A | | 5/1992 | Geyer et al. |
| 6,268,355 B1 | * | 7/2001 | Mizobuchi ............. A61K 47/14 514/165 |
| 6,306,843 B1 | * | 10/2001 | Burghart ............... A61K 9/0014 514/159 |
| 8,303,741 B2 | * | 11/2012 | Kabuto ..................... A61J 3/06 156/219 |

FOREIGN PATENT DOCUMENTS

| | | |
|---|---|---|
| CN | 102218088 A | 10/2011 |
| EP | 0920869 A1 | 6/1999 |
| GB | 873526 A | 7/1961 |
| JP | 2005082488 A | 3/2005 |
| WO | 0209666 A1 | 2/1991 |
| WO | 9101761 A1 | 2/1991 |
| WO | 9208445 A1 | 5/1992 |
| WO | 2011076401 A1 | 6/2011 |
| WO | 2012/174731 A1 | 12/2012 |

OTHER PUBLICATIONS

Lan et al, "Antitumor Effect of Aspirin in Glioblastoma Cells by Modulation of ß-Catenin/T-Cell Factor-Mediated Transcriptional Activity," Journal of Neurosurgery, vol. 115, pp. 780-788 (2011).
Mahon et al, "Saccharin: A Lead Compound for Structure-Based Drug Design of Carbonc Anhydrase IX Inhibitors," Bioorganic and Medicinal Chemistry, vol. 23, pp. 849-854 (2015).
McIntosh, "Could Saccharin Be Used to Treat Aggressive Cancers," Medical News Today, Published Mar. 23, 2015; Downloaded from http://www.medicalnewstoday.com/articles/291284.php.
Tsen et al, "Triacetin-Based Acetate Supplementation as a Chemotherapeutic Adjuvant Therapy in Glioma," Int J Cancer, vol. 134, No. 6, pp. 1300-1310 (2014).
Brown, "Characteisation of the Effects of Chronic Aspirin Treatment on the Viability and Proliferation of Stage 4 Glioblastoma Cells," the UCLan Journal of Undergraduate Research, vol. 6, Issue 2, pp. 1-14 (2013).
Gyory et al, "Effect of Particle Size on Aspirin-Induced Gastrointestinal Bleeding," The Lancet, pp. 300-302 (1968).
IARC Monographs, "Saccharin and Its Salts," vol. 73.
Jaworski et al, "Triacetin Treatment for Brain Cancer Cells," UVM Office of Technology Commercialization.
Int'l Search Report dated Mar. 29, 2016 in Int'l Application No. PCT/GB2015/054129.
Written Opinion dated Mar. 29, 2016 in Int'l Application No. PCT/GB2015/054129.

\* cited by examiner

*Primary Examiner* — Heidi Reese
(74) *Attorney, Agent, or Firm* — Panitch Schwarze Belisario & Nadel LLP; Lars H. Genieser

(57) ABSTRACT

A liquid composition contains a salicylate compound (e.g. aspirin), glycerin triacetate, saccharin. The salicylate compound is soluble in the composition, which is particularly suitable for oral, parenteral or pulmonary administration.

18 Claims, 18 Drawing Sheets

SALICYLATE COMPOUND COMPOSITION

CROSS-REFERENCE TO RELATED APPLICATION

This application is a Section 371 of International Application No. PCT/GB2015/054129, filed Dec. 22, 2015, which was published in the English language on Jun. 30, 2016, under International Publication No. WO 2016/102959 A1, and the disclosure of which is incorporated herein by reference.

FIELD OF INVENTION

The present invention relates to a stable salicylate compound composition, e.g. aspirin composition, in liquid form, in particular which is suitable for oral use, intravenous administration or inhalation.

BACKGROUND

Aspirin (acetylsalicylic acid) has been widely used as an analgesic to relieve minor aches and pains, as an antipyretic to reduce fever, and as an anti-inflammatory medication. Aspirin also has a 'COX' mediated antiplatelet effect by inhibiting the production of thromboxane, which under normal circumstances binds platelet molecules together to create a patch over damaged walls of blood vessels. Because the platelet patch can become too large and also block blood flow, locally and downstream, aspirin is also used long-term, at low doses, to help prevent heart attacks, strokes, and blood clot formation in people at high risk of developing blood clots. Also, low doses of aspirin may be given immediately after a heart attack to reduce the risk of another heart attack or the death of cardiac tissue. There is also growing evidence that aspirin can effectively prevent and slow the growth of cancers, in particular gastrointestinal cancers.

For example, Garcia-Albenix et al. (incorporated herein by reference) demonstrated that daily ingestion of aspirin over an 8-10 year period, at any dose, reduced the risk of colorectal cancer ('CRC') by an impressive 24% and CRC-associated mortality by an even more impressive 35%.

In addition, Lan et al. ["Antitumor effect of aspirin in glioblastoma cells by modulation of β-catenin/T-cell factor-mediated transcriptional activity", J Neurosurg, 2011, Vol. 115, pp. 780-788, incorporated herein by reference] found that aspirin is a potent antitumour agent which exerts its antineoplastic action by inhibition of the β-catenin/TCF signalling pathway in glioma cells.

Other studies have also shown aspirin to be a potent antitumour agent in glioma cell lines [M. W. Brown, 'Characterisation Of The Effects Of Chronic Aspirin Treatment On The Viability And Proliferation Of Stage 4 Glioblastoma Cells', *Diffusion: the UCLan Journal of Undergraduate Research*, Vol. 6, Issue 2, December 2013; Aas et al., 'Growth inhibition of rat glioma cells in vitro and in vivo by aspirin', *Journal of Neuro-Oncology*, 1995, Vol. 24, Issue 2, pp. 171-180; Ning et al., 'Overexpression of S100A9 in human glioma and in-vitro inhibition by aspirin', *European Journal of Cancer Prevention*, 2013, Vol. 22, Issue 6, pp. 585-595; Hwang et al., 'Effect of aspirin and indomethacin on prostaglandin E2 synthesis in C6 glioma cells', *Kaohsiung J Med Sci*, 2004, Vol. 20, pp. 1-5; Okada et al., 'Integration of epidemiology, immunobiology, and translational research for brain tumors', *Ann N Y Acad Sci*, 2013, Vol. 1284, pp. 17-23; all incorporated herein by reference].

Aspirin has often been called the 'wonder drug' or 'miracle cure'. For the last quarter of a century it has been universally accepted that this Willow tree bark derivative is of great benefit in cardiovascular disease prevention and cerebrovascular disease prevention. Over the last decade there has been a growing 'evidence based' realisation that it can prevent cancer (e.g. gastrointestinal or "GI" tract cancer). This anti-cancer effect has been shown to reduce cancer mortality by around 20% (Rothwell et al., 'Effect of daily aspirin on long-term risk of death due to cancer: analysis of individual patient data from randomised trials', Lancet, 2011, Vol. 377, pp. 31-41, incorporated herein by reference).

The main drawback of aspirin is its ability to cause gastric mucosal damage, which is exacerbated by the presence of particulate aspirin. Lan et al. (supra) identified these side-effects as the limiting factor in the treatment of glioma with aspirin. Fully solubilised, particulate free aspirin would be expected to reduce the local cytotoxic irritant effect of aspirin.

All current 'stable' aspirin formulations, whether they are called dispersible, soluble or effervescent, are simply dispersible particle formats, which will settle out into particulate form soon after being dissolved.

K. D. Rainsford ('*Aspirin and Related Drugs*', 2004, incorporated herein by reference) discusses the first definitive evidence of the direct gastric irritant actions of aspirin particles on the gastric mucosa. This was shown in a variety of studies in the 1930s, which showed that particles of unsolubilised aspirin embedded in the gastric mucosa or surrounding ulcer sites (Douthwaite and Lintott, 'Gastroscopic observations of the gastric mucosa after use of aspirin', *Lancet*, 1938, Vol. 232, pp. 1222-1225; Hurst and Lintott, 'Aspirin as a cause of hematemesis', *Guy's Hosp Rep*, 1939, p. 173, both incorporated herein by reference). Further confirmation of this effect is seen in the image taken by D. J. Levy ('An aspirin tablet and gastric ulcer', *N Engl J Med*, 2000, Vol. 343, No. 12, p. 863, incorporated herein by reference).

Rainsford et al. ('Electronmicroscopic observations on the effects of orally administered aspirin and aspirin-bicarbonate mixtures on the development of gastric mucosal damage in the rat', *Gut*, 1975, Vol. 16(7), pp. 514-527, incorporated herein by reference) noted that "the absence of particles of the drug in the aspirin and bicarbonate mixtures is clearly a major factor. A consequence of this is that there would be an increase of the spread of the drug over the mucosal and gastric pit, thereby reducing the amount of drug in concentrated particles which seems important in the development of focal damage and development of gastric mucosal damage". This is further supported by three further studies by Jaiswal et al. (IUPHAR 9th Int. Conference of Pharmacology, 1984, incorporated herein by reference), Liversage et al. ('Drug particle size reduction for decreasing gastric irritation and enhanced absorption of Naproxen in rats', *Int J Pharm*, 1995, Vol. 125(2), pp. 309-313, incorporated herein by reference) and Gyory et al. ('Effect of particle size on aspirin-induced gastrointestinal bleeding', *Lancet*, Vol. 292, No. 7563, pp. 300-302, incorporated herein by reference). These all clearly show that there is a definite correlation between the size of the aspirin particle and the severity of the gastrointestinal irritation.

M. I. Grossman et al. ('Fecal Blood Loss Produced By Oral And Intravenous Administration Of Various Salicylates', *Gastroenterology*, 1961, Vol. 40, pp. 383-388, incorporated herein by reference) firmly supports the aspirin 'particle effect' as the cause of GI irritation. Grossman suggests that in order for intravenous aspirin to cause GI bleeding, there must be pre-existing damage. He states that "the gun must be loaded in order for an explosion to occur when salicylates pull the trigger".

This is further supported by a series of seven studies, all looking at the effect of intravenous, subcutaneous or intrajejunal aspirin on the gastric mucosa. Each of these notes that the aspirin given at varying doses (some of which are extremely high) has a significant effect on systemic COX and prostaglandin production. In each case it is stated that despite having this systemic effect the only route of administration that causes gastrointestinal problems is where there is direct contact with the gastric mucosa. They all conclude that the effects seen are therefore due to direct contact 'particle' effect rather than 'COX' mediated systemic effects. The systemic COX effect is not a factor causing the GI side-effects of aspirin but rather exacerbates any bleeding from a pre-existing lesion, due to the COX-mediated anti-platelet effect. [Kevin et al., 'Acute effect of systemic aspirin on gastric mucosa in man', *Digestive Diseases and Sciences*, 1980, Vol. 25, Issue 2, pp 97-99; Cooke et al., 'Failure of intravenous aspirin to increase gastrointestinal blood loss', *British medical journal*, 1969; Vol. 3(5666), pp. 330-332; Wallace et al., 'Adaptation of rat gastric mucosa to aspirin requires mucosal contact' *Am J Physiol*, 1995, Vol. 268, G134-8; Cryer et al. 'Effects of low dose daily aspirin therapy on gastric, duodenal and rectal prostaglandin levels and on mucosal injury in healthy humans', *Gastroenterology*, 1999, Vol. 117, pp. 17-25; Lichtenberger et al., 'Where is the evidence that cyclooxygenase inhibition is the primary cause of nonsteroidal anti-inflammatory drug (NSAID)-induced gastrointestinal injury? Topical injury revisited', *Biochemical Pharmacology*, 2001, Vol. 61, pp. 631-637; Ligumsky M et al., 'Aspirin can inhibit gastric mucosal cyclo-oxygenase without causing lesions in the rat', *Gastroenterology*, 1983, Vol. 84, pp 756-61; and Zhao et al., 'Clinical Research Feasibility of intravenous administration of aspirin in acute coronary syndrome', *Journal of Geriatric Cardiology*, 2008, Vol. 5 No. 4, pp. 212-916, all incorporated herein by reference].

The presence of aspirin particles, in contact with the stomach lining, seems to be essential for the causation of aspirin GI irritation. This is not the case for the other NSAID's where the systemic COX effect is sufficient to induce GI injury (Mashita et al., 'Oral but not parenteral aspirin upregulates COX-2 expression in rat stomachs: a relationship between COX-2 expression and PG deficiency', Digestion, 2006, Vol. 73(2-3), pp. 124-32, incorporated herein by reference).

The study by Mashita et al. (ibid.) shows that while both Indomethacin (a 'new' NSAID) and aspirin both decrease PGE2 when given either orally or subcutaneously, only Indomethacin caused gastric damage via both administration routes. Aspirin only caused damage when given orally. They conclude that Aspirin caused damage due to topical irritation, while Indomethacin caused damage due to its systemic effect. This highlights the uniqueness of aspirin and distinguishes it from all other NSAIDs.

It is therefore clear that the direct topical irritation of aspirin particles on the gastric mucosa causes the damage leading to the side effects seen when taking oral aspirin. It follows that if the particles are removed by producing a stable, fully solubilised liquid aspirin, the adverse GI side effects will be significantly reduced or even totally eliminated.

Aspirin is generally only administered orally in solid form, i.e. tablets, granules etc., because of the instability of aspirin in solution or liquid form. Aspirin is not soluble and stable in water, or in any of the common solvents used in oral pharmaceuticals, such as propylene glycol, ethanol and glycerol. Aspirin is rapidly hydrolyzed to acetic and salicylic acids which results in a major loss of its pharmacological activity. Thus, the shelf life of aspirin in such solvents is far too short to permit the development of a stable aspirin solution suitable for commercial use. Water alone is not the only contributor to aspirin degradation in solution. Aspirin will also degrade by hydrolysis, glycolysis and trans-esterification, all of which will be promoted by any pH higher than about 3.5. There is a need for a stable and soluble aspirin composition in liquid form which can be taken orally.

Furthermore, other modes of administration suited to liquid drug compositions are at present not accessible by aspirin due to the instability in solution or liquid form and the difficulty in achieving complete solubilisation. For example, it is desirable to provide a stable aspirin composition, preferably containing completely solubilised aspirin, which may be administered to the bloodstream, e.g. intravenously or intraarterially, or may be administered to the lungs by inhalation, e.g. of a vapour or aerosol.

One particular advantageous use of a stable liquid aspirin composition is to orally give to stroke or heart attack victims, e.g. immediately after an attack, where it is often impossible for the patient to take aspirin in solid form. Other advantages include convenience, speed and completeness of absorption (increased bioavailability) and reduced gastric irritation. In addition, for elderly patients or patients suffering from Dysphagia (swallowing difficulties), it may be impossible or dangerous to administer solid aspirin orally. A stable liquid composition would address this problem.

Other salicylate compounds present problems associated with achieving a stable liquid composition in which the salicylate compound is fully solubilised. For example, stable liquid compositions of Diflunisal (2',4'-difluoro-4-hydroxybiphenyl-3-carboxylic acid), Triflusal (2-acetyloxy-4-(trifluoromethyl)benzoic acid), Salsalate (2-(2-hydroxybenzoyl)oxybenzoic acid) and salicylic acid itself (2-hydroxybenzoic acid) may also be desirable.

WO 91/01761 describes shelf-stable solutions of aspirin in DEET, which may also include glycerin triacetate as a co-solvent.

EP 0 920 862 describes solutions of aspirin with at least one substance selected from an ester of an organic acid, a glycerol fatty acid ester, silicon oil and hydrocarbon oil.

U.S. Pat. No. 6,306,843 describes stable aspirin solutions in a non-aqueous organic solvent, which include a cyclic acid imide and/or a sulfaminic acid.

The compositions described in these documents however do not provide sufficient stability and/or contain non-GRAS or non-pharmaceutically licensed products which are unsuitable for human ingestion. There therefore remains a need for stable aspirin solutions offering extended shelf-life with increased solubility and stability of the dissolved compound, which are suitable for therapeutic use in humans, particularly by oral administration.

SUMMARY OF THE INVENTION

In one aspect of the present invention there is provided a liquid composition comprising a salicylate compound, a glycerol derivative, and a saccharin compound.

The composition may further comprise a flavouring agent, which may comprise or consist of mint oil.

The composition provides a stable, liquid form of fully solubilised salicylate compound. As a result, the GI irritant side-effects discussed above are dramatically reduced, avoided, ameliorated or eliminated. Furthermore the liquid form provides a very easily administered composition. The components of the composition are pharmaceutically acceptable and provide a composition safe for use in the therapeutic treatment of humans.

The salicylate compound may be selected from the group consisting of: aspirin, triflusal, diflunisal, salsalate and salicylic acid. In preferred embodiments the salicylate compound is aspirin.

The glycerol derivative may be a glycerol derivative as described herein. In preferred embodiments the glycerol derivative is glycerin triacetate.

The saccharin compound may be a saccharin compound as described herein. In preferred embodiments the saccharin compound is saccharin.

In some embodiments the composition comprises or consists of a salicylate compound, glycerin triacetate, and saccharin. In some preferred embodiments the composition comprises or consists of aspirin, glycerin triacetate, and saccharin. In some embodiments the composition may comprise or consist of aspirin, glycerin triacetate, saccharin and a flavouring agent.

In some embodiments the concentration of the salicylate compound, preferably aspirin, may be 0.5 to 3 wt % and/or the concentration of the glycerol derivative, preferably glycerin triacetate, may be 94 to 99 wt %. In some embodiments the concentration of saccharin compound, preferably saccharin, may be 0.1 to 3 wt %.

For the avoidance of doubt, the components are present in the composition such that the total amount is equal to 100 wt %. For example, for a composition consisting of salicylate compound, glycerol derivative and saccharin compound, there may be 0.5 to 3 wt % salicylate compound, preferably aspirin, and 0.1 to 3 wt % saccharin compound, preferably saccharin. The glycerol derivative will then make up the balance of the composition to 100 wt %.

The glycerol derivative, e.g. glycerin triacetate, may be obtained or obtainable by a purification process. This process may be suitable to remove water or other impurities from the glycerol derivative. For example, the glycerol derivative may be treated by distillation and/or by passing through activated earth.

The glycerol derivative, e.g. glycerin triacetate, may be obtained or be obtainable by passing through activated earth.

In some embodiments the composition may have a salicylate compound, e.g. aspirin, degradation rate at 25° C. of less than 0.04%/day and/or less than 0.006 mg/g/day. In some embodiments the composition may have a salicylate compound, e.g. aspirin, degradation rate at 25° C. of less than 0.02%/day and/or less than 0.004 mg/g/day.

The composition may be free of particulates. The salicylate compound may be completely soluble in the liquid composition. In some embodiments, greater than 90% of the total amount of salicylate compound, preferably aspirin, in the composition is fully dissolved, for example at least 95%, at least 96%, at least 97%, at least 98%, at least 99% or at least 99.9%. In some embodiments 100% of the total salicylate compound is fully dissolved.

The composition may be suitable for oral use, or formulated for intravenous or intra-arterial administration or formulated for inhalation or insufflation administration. The composition may be a pharmaceutical composition or medicament.

In another aspect of the present invention a method of preparing or producing a liquid composition is provided, the method comprising admixing a salicylate compound, glycerol derivative, and a saccharin compound. The method may further comprise admixing a flavouring agent, e.g. mint oil.

The method may comprise comprising the steps of:
(a) adding the salicylate compound and saccharin compound to the glycerin derivative;
(b) optionally adding a flavouring agent; and
(b) mixing until fully dissolved.

The mixing may be performed by sonication of the liquid composition.

The salicylate compound may be selected from the group consisting of: aspirin, triflusal, diflunisal, salsalate and salicylic acid. In preferred embodiments the salicylate compound is aspirin.

The glycerol derivative may be a glycerol derivative as described herein. In preferred embodiments the glycerol derivative is glycerin triacetate.

The saccharin compound may be a saccharin compound as described herein. In preferred embodiments the saccharin compound is saccharin.

In some embodiments the method comprises admixing aspirin, glycerin triacetate and saccharin.

In some embodiments the concentration of the salicylate compound may be 0.5 to 3 wt % and/or the concentration of the glycerol derivative, preferably glycerin triacetate, may be 94 to 99 wt %.

In some embodiments the concentration of saccharin compound, preferably saccharin, is 0.1 to 3 wt %.

In another aspect of the present invention a packaged article comprising the liquid composition of the present invention is sealed therein is provided. The packaged article may be a bottle, pipette, syringe, vial, sachet, stick shot and liquid gel capsule.

The Blow-Fill-Seal (BFS) method may be used to manufacture the packaged article.

In another aspect of the present invention a method of taking aspirin which comprises orally administering a stable liquid composition according to the present invention is provided.

In another aspect of the present invention a method of taking aspirin which comprises oral, rectal, nasogastric, parenteral (e.g. intravenous or intrarterial), inhalation or insufflation administration of the liquid composition according to the present invention is provided.

In another aspect of the present invention a liquid composition according to the present invention is provided for use in a method of medical treatment.

In another aspect of the present invention the use of a salicylate compound or glycerol derivative or saccharin compound in the manufacture of a medicament or pharmaceutical composition according to the present invention for use in a method of medical treatment is provided.

In another aspect of the present invention a method of treatment of a disease or disorder is provided, the method comprising administering to a subject in need of treatment the composition according to the present invention, thereby treating the subject.

In some embodiments the method of medical treatment involves oral, rectal, nasogastric, parenteral (e.g. intravenous or intrarterial), inhalation or insufflation administration of the liquid composition.

In some embodiments the method of medical treatment involves the treatment or prevention of a cardiovascular disease, cerebrovascular disease or cancer.

The cardiovascular disease may be selected from angina pectoris; heart failure (HF); left or right ventricular failure; pulmonary heart disease; ischaemic heart disease (IHD); cardiomyopathy; cardiac dysrhythmia; stenosis of a heart valve; hypertrophic cardiomyopathy (HCM); coronary heart disease; paediatric cardiovascular disease (e.g. Kawasaki disease); and congenital heart disease.

The cerebrovascular disease may be selected from thrombotic and embolic stroke, cerebral ischaemia, brain ischaemia, transient ischaemic attack (TIA), and vascular dementia.

The cancer may be a cancer occurring in the central nervous system, a brain cancer or glioma.

The cancer may be a cancer of the gastrointestinal tract.

We have now surprisingly discovered an aspirin composition which overcomes or significantly reduces at least one of the aforementioned problems.

Accordingly, in one aspect the present invention provides a stable liquid composition comprising aspirin, glycerine triacetate, saccharin and an optional flavouring agent.

In another aspect the invention further provides a packaged article comprising a stable liquid composition comprising aspirin, glycerine triacetate, saccharin and an optional flavouring agent, which is sealed therein In another aspect the invention yet further provides a method of taking aspirin which comprises orally administering a stable liquid composition comprising aspirin, glycerine triacetate, saccharin and an optional flavouring agent.

In another aspect the invention still further provides a stable liquid composition comprising aspirin, glycerine triacetate, saccharin and an optional flavouring agent for use by oral administration as an analgesic, antipyretic, anti-inflammatory and/or antiplatelet.

In another aspect the invention even further provides the use of a composition comprising or consisting of glycerine triacetate, saccharin and an optional flavouring agent to produce a stable aspirin solution.

The following numbered paragraphs contain statements of broad combinations of the inventive technical features herein disclosed:—

1. A stable liquid composition comprising aspirin, glycerine triacetate, saccharin and an optional flavouring agent.
2. The composition according to paragraph 1 wherein the concentration of the aspirin is 0.5 to 3% and/or the concentration of the glycerin triacetate is 94 to 99%.
3. The composition according to either one of paragraphs 1 and 2 wherein the concentration of the saccharin is 0.1 to 3%.
4. The composition according to any one of the preceding paragraphs wherein the flavouring agent comprises or consists of mint oil.
5. The composition according to any one of the preceding paragraphs wherein the composition consists of aspirin, glycerine triacetate, saccharin and an optional flavouring agent.
6. The composition according to any one of the preceding paragraphs wherein the glycerine triacetate is obtainable by passing through activated earth.
7. The composition according to any one of the preceding paragraphs having an aspirin degradation rate at 25° C. of less than 0.04%/day and/or less than 0.006 mg/g/day.
8. The composition according to paragraph 7 having an aspirin degradation rate at 25° C. of less than 0.02%/day and/or less than 0.004 mg/g/day.
9. The composition according to any one of the preceding paragraphs which is free of particulates and/or the aspirin is completely soluble.
10. The composition according to any one of the preceding paragraphs which is suitable for oral use.

11. A packaged article comprising the composition as defined in any one of the preceding paragraphs which is sealed therein.
12. The packaged article according to paragraph 11 selected from the group consisting of a bottle, pipette, syringe, vial, sachet, stick shot and liquid gel capsule.
13. A method of taking aspirin which comprises orally administering a stable liquid composition comprising aspirin, glycerine triacetate, saccharin and an optional flavouring agent.
14. A stable liquid composition comprising aspirin, glycerine triacetate, saccharin and an optional flavouring agent for use by oral administration as an analgesic, antipyretic, anti-inflammatory and/or antiplatelet.
15. The use of a composition comprising or consisting of glycerine triacetate, saccharin and an optional flavouring agent to produce a stable aspirin solution.

DESCRIPTION

The inventors have discovered that by formulating a salicylate compound together with a glycerol derivative and a saccharin compound that a highly stable liquid salicylate formulation can be provided.

Salicylate Compound

The term "salicylate compound" as used herein refers to compounds according to Formula (I):

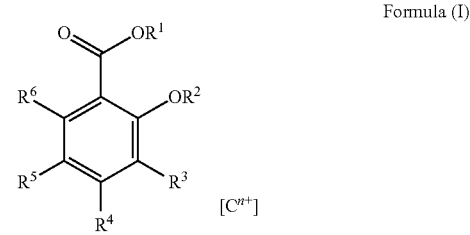

wherein:

$R^1$ is a negative charge, or is independently selected from the group consisting of
—H,
—$R^A$
—OH, —$OR^A$, —$CF_3$, —$OCF_3$,
—COH, —$COR^A$, —COOH, —$COOR^A$,
—$NH_2$, —$NHR^A$, —$NR^A_2$ and —$NR^B_2$;

$R^2$ is independently selected from the group consisting of
—H,
—$R^A$,
—OH, —$OR^A$, —$CF_3$, —$OCF_3$,
—COH, —$COR^A$, —COOH, —$COOR^A$,
—$NH_2$, —$NHR^A$, —$NR^A_2$, —$NR^B_2$, and
-Q;

$R^3$—$R^6$ are each independently selected from the group consisting of
—H,
—F, —Cl, —Br, —I,
—$R^A$,
—OH, —$OR^A$, —$CF_3$, —$OCF_3$,
—CN, —$NO_2$,
—COH, —$COR^A$, —COOH, —$COOR^A$,
—$NH_2$, —$NHR^A$, —$NR^A_2$, —$NR^B_2$,
—$SO_3H$, —$S(O)R^A$ and —$S(O_2)R^A$;

Q is

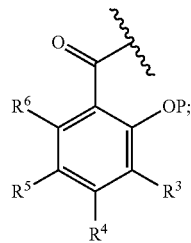

and P is independently selected from —H, linear or branched $C_{1-4}$ alkyl, alkenyl or alkynyl, or —COR$^A$;
wherein —R$^A$ is independently selected from the group consisting of
  linear or branched $C_{1-4}$alkyl, alkenyl or alkynyl,
  phenyl optionally substituted with one or more groups —R$^D$,
  benzyl optionally substituted with one or more groups —R$^D$,
  —COOH, —COOR$^C$, —C(O)R$^D$, —NH$_2$, —NHR$^C$ or —NR$^C_2$;
—R$^D$ is independently selected from
  linear or branched $C_{1-4}$alkyl, alkenyl or alkynyl,
  —F, —Cl, —Br, —I,
  —OH, —OR$^C$, —CF$_3$, —OCF$_3$,
  —CN, —NO$_2$,
  —COH, —COR$^C$, —COOH, —COOR$^C$,
  —NH$_2$, —NHR$^C$, —NR$^C_2$, —NR$^B_2$,
  —S(O)R$^C$ and —S(O$_2$)R$^C$;
—R$^C$ is independently selected from linear or branched $C_{1-4}$alkyl, alkenyl or alkynyl;
—NR$^B_2$ is independently selected from the group consisting of azetidino, imidazolidino, pyrazolidino, pyrrolidino, piperidino, piperazino, N—C$_{1-4}$alkyl-piperazino, morpholino, azepino or diazepino, optionally substituted with one or more groups selected from linear or branched $C_{1-4}$ alkyl, alkenyl or alkynyl, phenyl and benzyl; and
[C$^+$] is an optional counter-cation selected from the group consisting of alkali metal ions, alkaline earth metal ions, transition metal ions, Al$^{3+}$, ammonium or substituted ammonium ion and NO$_2^+$.

The Group —R$^1$

In some embodiments, R$^1$ is a negative charge, or is independently selected from the group consisting of
  —H,
  —R$^A$
  —COH, —COR$^A$, —COOH, —COOR$^A$,
  —NH$_2$, —NHR$^A$, —NR$^A_2$ and —NR$^B_2$.

In some embodiments, R$^1$ is a negative charge, or is independently selected from the group consisting of —H and —R$^A$.

In some embodiments, R$^1$ is a negative charge, or is independently selected from the group consisting of
  —H,
  linear or branched $C_{1-4}$alkyl, alkenyl or alkynyl,
  phenyl optionally substituted with one or more groups —R$^D$,
  benzyl optionally substituted with one or more groups —R$^D$,
  and —C(O)R$^C$.

In some embodiments, R$^1$ is a negative charge, —H, or linear or branched $C_{1-4}$alkyl, alkenyl or alkynyl.

In some embodiments, R$^1$ is a negative charge.
In some embodiments, R$^1$ is —H.
When R$^1$ is a negative charge, counter-cation [C$^{n+}$] is present.

The Group —R$^2$
In some embodiments, R$^2$ is independently selected from the group consisting of
  —H,
  —R$^A$,
  —COH, —COR$^A$, —COOH, —COOR$^A$, and
  -Q.

In some embodiments, R$^2$ is independently selected from the group consisting of —COH, —COR$^A$; and -Q.
In some embodiments, R$^2$ is independently selected from the group consisting of —H, —COR$^C$, and -Q.
In some embodiments, R$^2$ is independently selected from the group consisting of —H, —C(O)CH$_3$, and -Q.
In some embodiments, R$^2$ is independently —H.
In some embodiments, R$^2$ is independently —C(O)CH$_3$.
In some embodiments, R$^2$ is independently -Q.

The Groups R$^3$-R$^6$
In some embodiments, R$^3$-R$^6$ are each independently selected from
  —H,
  —F, —Cl, —Br,
  —CN, —NO$_2$,
  —R$^A$,
  —OH, —OR$^A$, —CF$_3$ and —OCF$_3$.

In some embodiments, R$^3$-R$^6$ are each independently selected from
  —H,
  —F, —Cl,
  —R$^A$,
  —OH, —OR$^A$ and —CF$_3$.

In some embodiments, R$^3$-R$^6$ are each independently selected from
  —H,
  phenyl optionally substituted with one or more groups —R$^D$,
  and —CF$_3$.

In some embodiments, R$^4$ is independently —CF$_3$, wherein R$^3$, R$^5$ and R$^6$ are preferably each independently —H.

In some embodiments, R$^5$ is phenyl optionally substituted with one or more groups —R$^D$, wherein —R$^D$ is preferably —F, and R$^3$, R$^4$ and R$^6$ are preferably each independently —H.

In some embodiments, each of R$^3$-R$^6$ is independently —H.

In some embodiments, the salicylate compound is aspirin (2-(acetoxy)benzoic acid), according to Formula (Ia):

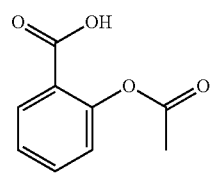

Formula (Ia)

In some embodiments, the salicylate compound is triflusal (2-acetyloxy-4-(trifluoromethyl)benzoic acid), according to Formula (Ib):

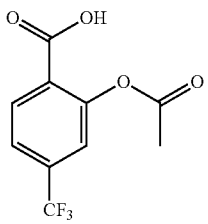

In some embodiments, the salicylate compound is diflunisal (2',4'-difluoro-4-hydroxybiphenyl-3-carboxylic acid), according to Formula (Ic):

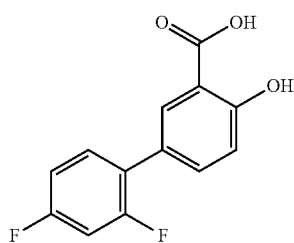

In some embodiments, the salicylate compound is salsalate (2-(2-hydroxybenzoyl)oxybenzoic acid), according to Formula (Id):

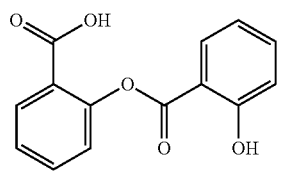

In some embodiments, the salicylate compound is salicylic acid (2-Hydroxybenzoic acid), according to Formula (Ie):

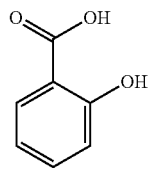

In preferred embodiments the salicylate compound is aspirin.

Glycerol Derivative

The term "glycerol derivative" as used herein refers to compounds according to Formula (II):

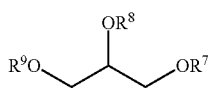

wherein:
$R^7$-$R^9$ are each independently selected from the group consisting of
—H,
—$R^A$,
—COH, —CO$R^A$, —COOH, —COO$R^A$,
—NH$_2$, —NH$R^A$, —N$R^A{}_2$, —N$R^B{}_2$,
—S(O)$R^A$ and —S(O$_2$)$R^A$;
wherein —$R^A$ is independently selected from the group consisting of
linear or branched $C_{1-4}$alkyl, alkenyl or alkynyl,
phenyl optionally substituted with one or more groups —$R^D$,
benzyl optionally substituted with one or more groups —$R^D$,
—COOH, —COO$R^C$, —C(O)$R^C$, —NH$_2$, —NH$R^C$ or —N$R^C{}_2$,
—$R^D$ is independently selected from
linear or branched $C_{1-4}$alkyl, alkenyl or alkynyl,
—F, —Cl, —Br, —I,
—OH, —O$R^C$, —CF$_3$, —OCF$_3$,
—CN, —NO$_2$,
—COH, —CO$R^C$, —COOH, —COO$R^C$,
—NH$_2$, —NH$R^C$, —N$R^C{}_2$, —N$R^B{}_2$,
—S(O)$R^C$ and —S(O$_2$)$R^C$;
—$R^C$ is independently selected from linear or branched $C_{1-4}$alkyl, alkenyl or alkynyl; and
—N$R^B{}_2$ is independently selected from the group consisting of azetidino, imidazolidino, pyrazolidino, pyrrolidino, piperidino, piperazino, N—$C_{1-4}$alkyl-piperazino, morpholino, azepino or diazepino, optionally substituted with one or more groups selected from linear or branched $C_{1-4}$alkyl, alkenyl or alkynyl, phenyl and benzyl.

The Groups $R^7$-$R^9$

In some embodiments, $R^7$-$R^9$ are each independently selected from the group consisting of —H and —$R^A$.

In some embodiments, $R^7$-$R^9$ are each independently selected from the group consisting of —H, linear or branched $C_{1-4}$alkyl, alkenyl or alkynyl, and —C(O)$R^C$.

In some embodiments, $R^7$-$R^9$ are each independently selected from the group consisting of —H, and —C(O)$R^C$, wherein $R^C$ is preferably methyl.

In some embodiments, one of $R^7$-$R^9$ is —H and the other two are —C(O)$R^C$, wherein $R^C$ is preferably methyl.

In some embodiments, one of $R^7$-$R^9$ is —C(O)$R^C$ and the other two are —H, wherein $R^C$ is preferably methyl.

In some embodiments, $R^7$-$R^9$ are each selected from —C(O)$R^C$, wherein $R^C$ is preferably methyl.

In some preferred embodiments, the glycerol derivative is glycerin triacetate (also known as glyceryl triacetate, GTA, or triacetin, or 1,3-Diacetyloxypropan-2-yl acetate) according to Formula (IIa):

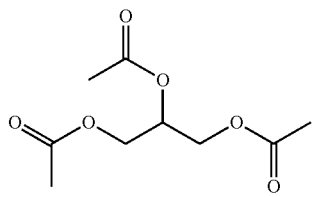

Glycerin triacetate is an FDA approved food additive with "generally regarded as safe" status that has been tested for parenteral nutrition in a wide variety of species with no adverse effects. Glycerin triacetate is also used as a vaporising agent in e-cigarettes and is regarded as safe when used in that context.

The glycerin triacetate (also commonly known as glycerine triacetate, glyceryl triacetate, or triacetin) used herein acts as a solvent for the aspirin or salicylate compound and can give clear aspirin or salicylate compound solutions. Food grade glycerin triacetate may be employed, but it is preferably subjected to further purification processes, e.g. additional distillation steps. In one preferred embodiment, the glycerin triacetate is passed through activated earth, such as a column or fixed bed thereof. The viscosity of glycerin triacetate can be reduced by mixing with a suitable solvent, such as ethanol, prior to passing through the activated earth. The solvent can then be removed by using vacuum distillation followed by steam distillation, preferably to levels below 1 ppm of solvent in the glycerine triacetate.

Saccharin Compound

The term "saccharin compound" as used herein refers to compounds according to Formula (III):

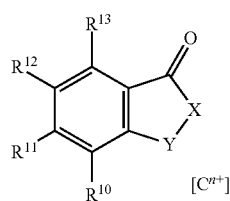

Formula (III)

wherein:
$R^{10}$-$R^{13}$ are each independently selected from the group consisting of
    —H,
    —F, —Cl, —Br, —I,
    —$R^A$,
    —OH, —$OR^A$, —$CF_3$, —$OCF_3$,
    —CN, —$NO_2$,
    —COH, —$COR^A$, —COOH, —$COOR^A$,
    —$NH_2$, —$NHR^A$, —$NR^A_2$, —$NR^B_2$,
    —$SO_3H$, —$S(O)R^A$, —$S(O_2)R^A$, and
    —W;
X is independently selected from the group consisting of
    —$N^\ominus$, —NH and —$NR^A$,
Y is independently selected from $S(O_2)$;
wherein —$R^A$ is independently selected from the group consisting of
    linear or branched $C_{1-4}$alkyl, alkenyl or alkynyl,
    phenyl optionally substituted with one or more groups —$R^D$,
    benzyl optionally substituted with one or more groups —$R^D$,
    —COOH, —$COOR^C$, —$C(O)R^C$, —$NH_2$, —$NHR^C$ or —$NR^C_2$;
—$R^D$ is independently selected from
    linear or branched $C_{1-4}$alkyl, alkenyl or alkynyl,
    —F, —Cl, —Br, —I,
    —OH, —$OR^C$, —$CF_3$, —$OCF_3$,
    —CN, —$NO_2$,
    —COH, —$COR^C$, —COOH, —$COOR^C$,
    —$NH_2$, —$NHR^C$, —$NR^C_2$, —$NR^B_2$,
    —$S(O)R^C$ and —$S(O_2)R^C$;
—$R^C$ is independently selected from linear or branched $C_{1-4}$ alkyl, alkenyl or alkynyl;

—$NR^B_2$ is independently selected from the group consisting of azetidino, imidazolidino, pyrazolidino, pyrrolidino, piperidino, piperazino, N—$C_{1-4}$alkyl-piperazino, morpholino, azepino or diazepino, optionally substituted with one or more groups selected from linear or branched $C_{1-4}$alkyl, alkenyl or alkynyl, phenyl and benzyl;
—W is the group

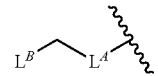

wherein $L^A$ is independently selected from a 5- or 6-membered heteroaromatic group and $L^B$ is independently selected from a 5- or 6-membered monosaccharide moiety; and
$[C^+]$ is an optional counter-cation selected from the group consisting of alkali metal ions, alkaline earth metal ions, transition metal ions, $Al^{3+}$, ammonium or substituted ammonium ion and $NO_2^+$.

The Group X

In some embodiments, X is independently selected from $N^\ominus$ and NH.

In some embodiments, X is independently $N^\ominus$ and $[C^{n+}]$ is a counter-cation selected from alkali metal ions and alkaline earth metal ions.

In some embodiments, X is independently $N^\ominus$ and $[C^{n+}]$ is a counter-cation selected from sodium and calcium ions.

In some embodiments, X is independently NH.

The Groups $R^{10}$-$R^{13}$

In some embodiments, $R^{10}$-$R^{13}$ are each independently selected from
    —H,
    —F, —Cl, —Br,
    —$R^A$,
    —OH, —$OR^A$, —$CF_3$, —$OCF_3$,
    —CN, —$NO_2$,
    —COH, —$COR^A$, —COOH, —$COOR^A$,
    —$NH_2$, —$NHR^A$, —$NR^A_2$, —$NR^B_2$, and
    —W.

In some embodiments, $R^{10}$-$R^{13}$ are each independently selected from
    —H,
    —F, —Cl, —Br,
    —$R^A$,
    —OH, —$OR^A$, —$CF_3$, —$OCF_3$, and
    —W.

In some embodiments, $R^{10}$-$R^{13}$ are each independently selected from
    —H,
    —F, —Cl,
    —$R^A$,
    —OH, —$OR^A$, and
    —W.

In some embodiments, $R^{10}$-$R^{13}$ are each independently selected from
    —H,
    —F, —Cl,
    linear or branched $C_{1-4}$alkyl, alkenyl, alkynyl,
    —OH, and
    —W.

In some embodiments, $R^{10}$-$R^{13}$ are each independently selected from
    —H,
    —F, —Cl, linear or branched $C_{1-4}$ alkyl, alkenyl, alkynyl and —OH.

In some embodiments, one of $R^{10}$-$R^{13}$ is independently —W and the remaining groups of $R^{10}$-$R^{13}$ are independently —H.

In some embodiments, $R^{11}$ is independently —W and $R^{10}$, $R^{12}$ and $R^{13}$ are each independently —H.

The Group $L^A$

In some embodiments, $L^A$ is a 5- or 6-membered heteroaromatic group independently selected from imidazolyl, pyrazolyl, oxazolyl, isooxazolyl, thiazolyl, isothiazolyl, dioxolanyl, dithiolanyl, triazolyl, furanyl, oxadiazolyl, thiadiazolyl, dithiazolyl, tetrazolyl, pyridinyl, pyranyl, thiopyranyl, diazinyl, oxazinyl, thiazinyl, dioxinyl, dithiinyl, triazinyl and tetrazinyl.

In some embodiments, $L^A$ is a 5-membered heteroaromatic group independently selected from imidazolyl, pyrazolyl, oxazolyl, isooxazolyl, thiazolyl, isothiazolyl, dioxolanyl, dithiolanyl, triazolyl, furanyl, oxadiazolyl, thiadiazolyl, dithiazolyl and tetrazolyl.

In some embodiments, $L^A$ is a 5-membered heteroaromatic group independently selected from triazolyl, furanyl, oxadiazolyl, thiadiazolyl and dithiazolyl.

In some embodiments, $L^A$ is a 5-membered heteroaromatic group independently selected from one of the following triazolyl moieties:

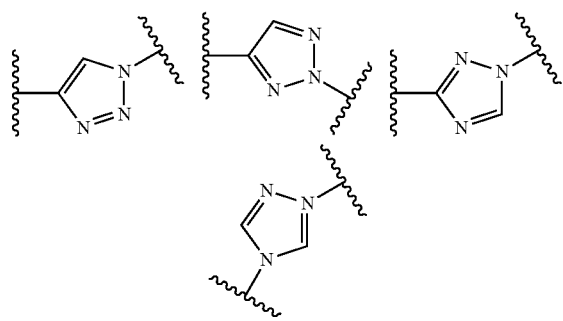

In some embodiments, $L^A$ is

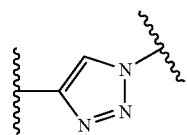 [SMILES: *c1cn(*)nn1]

The Group $L^B$

In some embodiments, $L^B$ is independently selected from ribofuranyl, glucopyranyl, galactopyranyl, mannopyranyl and allopyranyl.

In some embodiments, $L^B$ is the following 6-membered monosaccharide moiety:

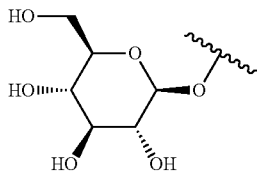

In some preferred embodiments, the saccharin compound is saccharin (2H-1$\lambda^6$,2-benzothiazol-1,1,3-trione), according to Formula (IIIa):

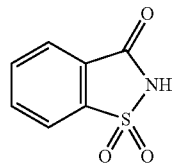

Formula (IIIa)

In some embodiments, the saccharin compound is a saccharide salt according to Formula (IIIb):

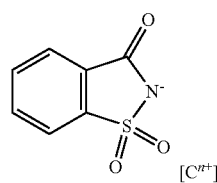

Formula (IIIb)

wherein [$C^{n+}$] is a counter-cation selected from the group consisting of alkali metal ions, alkaline earth metal ions, transition metal ions, $Al^{3+}$, ammonium or substituted ammonium ion and $NO_2^+$, more preferably sodium or calcium ion.

In some embodiments, the saccharin compound is a compound according to Formula (IIIc):

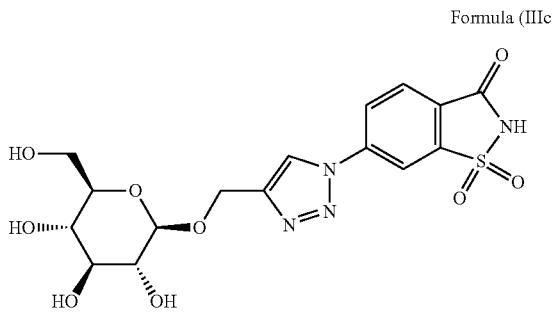

Formula (IIIc)

Any combination of salicylate compound, glycerol derivative and saccharin compound may be present, along with an optional flavouring agent, in the liquid compositions according to a first aspect of the invention.

In some embodiments, the glycerol derivative is a compound according to Formula (IIa), the saccharin compound is a compound according to Formula (IIIa) or (IIIb) and the salicylate compound is one or more salicylate compounds according to Formula (I).

In some embodiments, the glycerol derivative is a compound according to Formula (IIa), the saccharin compound is a compound according to Formula (IIIa) or (IIIb) and the salicylate compound is one or more salicylate compounds according to Formulae (Ia)-(Ie).

In some embodiments, the glycerol derivative is a compound according to Formula (IIa), the saccharin compound is a compound according to Formula (IIIa) or (IIIb) and the salicylate compound is a compound according to Formula (Ia).

Isomers

Certain of the compounds described above may exist in one or more particular geometric, optical, enantiomeric, diastereoisomeric, epimeric, atropic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

A reference to a class of structures may well include structurally isomeric forms falling within that class (e.g., $C_{1-7}$alkyl includes n-propyl and iso-propyl; butyl includes n-, iso-, sec-, and tert-butyl; methoxyphenyl includes ortho-, meta-, and para-methoxyphenyl).

However, reference to a specific group or substitution pattern is not intended to include other structural (or constitutional isomers) which differ with respect to the connections between atoms rather than by positions in space. For example, a reference to a methoxy group, —$OCH_3$, is not to be construed as a reference to its structural isomer, a hydroxymethyl group, —$CH_2OH$. Similarly, a reference to ortho-chlorophenyl is not to be construed as a reference to its structural isomer, meta-chlorophenyl.

The above exclusion does not pertain to tautomeric forms, for example, keto-, enol-, and enolate forms, as in, for example, the following tautomeric pairs: keto/enol (illustrated below), imine/enamine, amide/imino alcohol, amidine/amidine, nitroso/oxime, thioketone/enethiol, N nitroso/hydroxyazo, and nitro/aci-nitro.

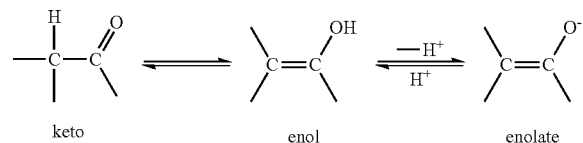

keto    enol    enolate

Note that specifically included in the term "isomer" are compounds with one or more isotopic substitutions. For example, H may be in any isotopic form, including $^1H$, $^2H$ (D), and $^3H$ (T); C may be in any isotopic form, including $^{12}C$, $^{13}C$, and $^{14}C$; O may be in any isotopic form, including $^{16}O$ and $^{18}O$; and the like.

Unless otherwise specified, a reference to a particular compound includes all such isomeric forms, including mixtures (e.g., racemic mixtures) thereof. Methods for the preparation (e.g., asymmetric synthesis) and separation (e.g., fractional crystallisation and chromatographic means) of such isomeric forms are known in the art or are readily obtained by adapting known methods in a known manner.

Salts

As explained above, the salicylate compound and/or the saccharin compound can be provided as salts. As such, in this specification the terms "salicylate compound" and "saccharin compound" include salts thereof.

It may be convenient or desirable to prepare, purify, and/or handle a corresponding salt of a compound, for example, a pharmaceutically-acceptable salt. Examples of pharmaceutically acceptable salts are discussed in Berge et al., 1977, "Pharmaceutically Acceptable Salts," J. Pharm. Sci., Vol. 66, pp. 1-19.

For example, when the salicylate compound or saccharin compound exists as an anion, or has a functional group which may be anionic (e.g., —COOH may be —COO$^-$), then a salt may be formed with a suitable cation (such as [$C^{n+}$] described above). Examples of suitable inorganic cations include, but are not limited to, alkali metal ions such as Na$^+$ and K$^+$, alkaline earth cations such as Ca$^{2+}$ and Mg$^{2+}$, and other cations such as Al$^{3+}$. Examples of suitable organic cations include, but are not limited to, ammonium ion (i.e., NH$_4^+$) and substituted ammonium ions (e.g., NH$_3$R$^+$, NH$_2$R$^{2+}$, NHR$^{3+}$, NR$^{4+}$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

If a compound is cationic, or has a functional group which may be cationic (e.g., —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous. Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, gluchephtonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

Unless otherwise specified, a reference to a particular compound also includes salt forms thereof.

Solvates and Hydrates

It may be convenient or desirable to prepare, purify, and/or handle a corresponding solvate of a compound. The term "solvate" is used herein in the conventional sense to refer to a complex of solute (e.g., compound, salt of compound) and solvent. If the solvent is water, the solvate may be conveniently referred to as a hydrate, for example, a mono-hydrate, a di hydrate, a tri-hydrate, etc.

Unless otherwise specified, a reference to a particular compound also includes solvate and hydrate forms thereof.

Prodrugs

It may be convenient or desirable to prepare, purify, and/or handle a compound, especially the salicylate compound, in the form of a prodrug. The term "prodrug," as used herein, pertains to a compound which, when metabolised (e.g., in vivo), yields the desired active compound. Typically, the prodrug is inactive, or less active than the desired active compound, but may provide advantageous handling, administration, or metabolic properties.

In one embodiment, the glycerin triacetate used herein may suitably comprise in the range from 0 to 1 wt %, preferably 0 to 0.5 wt %, more preferably 0 to 0.1 wt %, particularly 0 to 0.05 wt %, and especially 0 to 0.015% of glycerin monoacetate and/or glycerine diacetate.

The glycerin triacetate may also suitably comprise in the range from 0 to 100 ppm, preferably 0 to 20 ppm, more preferably 0 to 10 ppm, particularly 0 to 2 ppm, and especially 0 to 1 ppm of glycerine monoacetate and/or glycerine diacetate.

In one embodiment, the glycerin triacetate may suitably comprise in the range from 0 to 50 ppm, preferably 0 to 10 ppm, more preferably 0 to 5 ppm, particularly 0 to 1 ppm, and especially 0 to 0.5 ppm of glycerine.

The glycerin triacetate suitably comprises in the range from 0 to 100 ppm, preferably 0 to 20 ppm, more preferably 0 to 10 ppm, particularly 0 to 2 ppm, and particularly 0 to 1 ppm of non-polar materials, such as colour pigments and/or soaps.

In one preferred embodiment, the glycerin triacetate is substantially anhydrous, suitably comprising in the range from 0 to 0.5 wt %, preferably less than 0.3 wt %, more preferably less than 0.2 wt %, particularly less than 0.1 wt %, and especially less than 0.05 wt % of water.

A reduction in water content of the glycerin triacetate ensures a low water content in the composition. This provides increased stability of the liquid composition because salicylate compounds such as aspirin are vulnerable to hydrolysis in the presence of water to produce salicylic acid and other acids as by-products. If an aspirin composition contains 10 wt % salicylic acid with reference to the total amount of aspirin and salicylic acid present, the composition is no longer deemed to be pharmaceutically acceptable. Thus an increase in aspirin stability results in an extended shelf-life of the pharmaceutical composition.

Preferably the composition comprises at least 5 wt % glycerin triacetate, for example at least 10 wt %, at least 15 wt %, at least 20 wt % or at least 25 wt %. Most preferably, the composition comprises at least 90 wt % glycerin triacetate, for example at least 91 wt %, at least 92 wt %, at least 93 wt %, at least 94 wt %, at least 95 wt % or at least 96 wt %.

Preferably the composition comprises up to 99.9 wt % glycerin triacetate, for example up to 99 wt %, up to 98 wt %, up to 97 wt % or up to 96.5 wt %.

The concentration of the glycerin triacetate in the composition according to the invention is suitably in the range from 90 to 99%, preferably 94 to 98%, more preferably 95 to 97.5%, particularly 95.5 to 97%, and especially 96 to 96.5% by weight based on the total weight of the composition.

At this concentration of glycerin triacetate excellent solubilisation and stability of the salicylate compound is observed and a shelf-life of over 1 year, preferably about 18 months or 2 years, may be achieved. As used herein, "stability" refers to the resistance to degradation of the salicylate compound. Higher stability means that after a given period of time lower levels of contaminants will accumulate in the composition. These contaminants may be the products of the hydrolysis of the salicylate compound. The stability of a composition may be measured using the method described below.

Preferably the composition comprises at least 0.1 wt % salicylate compound, e.g. aspirin, for example at least 0.5 wt %, at least 1 wt %, at least 1.5 wt %, at least 2.0 wt % or at least 2.5 wt %. In this way a pharmaceutically effective amount of salicylate compound, e.g. aspirin may be provided in a small amount of liquid composition. Of course the necessary dose will depend on e.g. the disorder being treated, the identity of the patient etc. as explained further below.

Preferably the composition comprises up to 10 wt % salicylate compound, e.g. aspirin, for example up to 9 wt %, up to 8 wt %, up to 7 wt %, up to 6 wt %, up to 5 wt %, up to 4 wt %, up to 3 wt % or up to 2.5 wt %. In this way the stability and solubility of the salicylate compound, e.g. aspirin, in the composition is maximised.

When the concentration of salicylate compound, e.g. aspirin, exceeds this amount there is an increased risk that not all the aspirin in the liquid composition will be fully solubilised, which may lead to a granular precipitate having the disadvantages associated with solid aspirin compositions.

The concentration of the salicylate compound, e.g. aspirin, in the composition according to the invention is suitably in the range from 0.5 to 7%, preferably 1 to 5%, more preferably 2 to 3%, particularly 2.3 to 2.7%, and especially 2.4 to 2.6% by weight based on the total weight of the composition.

In one preferred embodiment, the salicylate compound is substantially anhydrous, suitably comprising in the range from 0 to 0.5 wt %, preferably less than 0.3 wt %, more preferably less than 0.2 wt %, particularly less than 0.1 wt %, and especially less than 0.05 wt % of water.

The composition may comprise at least 0.1 wt % saccharin, for example at least 0.2 wt %, at least 0.3 wt %, at least 0.4 wt %, at least 0.5 wt %, at least 0.6 wt %, at least 0.7 wt %, at least 0.8 wt % or at least 0.9 wt %. In this way, excellent stability and solubilisation of the salicylate compound is achieved.

The composition may comprise up to 5 wt % saccharin, for example up to 4 wt %, up to 3 wt %, up to 2 wt %, up to 1.5 wt %, up to 1.2 wt % or up to 1.1 wt %.

The concentration of the saccharin in the composition according to the invention is suitably in the range from 0.1 to 4%, preferably 0.4 to 3%, more preferably 0.7 to 1.5%, particularly 0.8 to 1.2%, and especially 0.9 to 1.1% by weight based on the total weight of the composition.

In one preferred embodiment, the saccharin compound is substantially anhydrous, suitably comprising in the range from 0 to 0.5 wt %, preferably less than 0.3 wt %, more preferably less than 0.2 wt %, particularly less than 0.1 wt %, and especially less than 0.05 wt % of water.

The composition according to the invention is preferably substantially anhydrous, suitably comprising in the range from 0 to 0.5 wt %, preferably less than 0.3 wt %, more preferably less than 0.2 wt %, particularly less than 0.1 wt %, and especially less than 0.05 wt % of water.

The composition according to the invention preferably comprises less than 0.5 wt % water, for example less than 0.4 wt %, less than 0.3 wt %, less than 0.2 wt %, or less than 0.1 wt % water. In some embodiments the composition according to the invention comprises less than 1000 ppm water, for example less than 900 ppm, less than 800 ppm, less than 700 ppm, less than 600 ppm or less than 500 ppm water.

As explained above, keeping the level of water in the composition low increases the stability of the salicylate compound in the composition thereby increasing the shelf-life.

The liquid composition of the invention may optionally also comprise one or more other pharmaceutically acceptable ingredients well known to those skilled in the art, including, but not limited to, pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavouring agents, and sweetening agents. The formulation may further comprise other active agents, for example, other therapeutic or prophylactic agents.

The term "pharmaceutically acceptable," as used herein, pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation without exerting a detrimental effect on the solubility or stability of the salicylate compound.

Suitable carriers, diluents, excipients, etc. can be found in standard pharmaceutical texts, for example, *Remington's Pharmaceutical Sciences,* 18th edition, Mack Publishing Company, Easton, Pa., 1990; and *Handbook of Pharmaceutical Excipients,* 5th edition, 2005.

The composition may also comprise an optional masking or flavouring agent. Suitable masking agents may mask or hide any objectionable flavour of the base composition. The flavouring agent preferably comprises any natural or synthetically prepared fruit or botanical flavouring agent, or mixtures thereof. Suitable natural or artificial fruit flavouring agents include lemon, orange, grapefruit, strawberry, banana, pear, kiwi, grape, apple, mango, pineapple, passion fruit, raspberry, and mixtures thereof. The fruit flavouring agent is suitably in anhydrous form such as dried juice or oil, preferably oil. Suitable botanical flavours include any member of the mint family such as spearmint, peppermint, watermint, apple mint; and other flavours such as Jamaica, marigold, *chrysanthemum*, tea, chamomile, ginger, valerian, yohimbe, hops, eriodictyon, *ginseng*, bilberry, rice, red wine, mango, peony, lemon balm, nut gall, oak chip, lavender, walnut, gentiam, luo han guo, cinnamon, *angelica*, aloe, agrimony, yarrow, and mixtures thereof. The botanical flavouring agent is suitably an anhydrous concentrate or an extract, for example in the form of oil or dried to form a powder.

The flavouring agent preferably comprises, consists essentially of, or consists of, mint flavouring agent, more preferably in the form of oil, particularly spearmint and/or peppermint oil, and especially spearmint oil.

The composition may comprise at least 0 wt %, for example at least 0.05 wt %, at least 0.06 wt %, at least 0.07 wt %, at least 0.08 wt %, at least 0.09 wt % or at least 0.1 wt % flavouring agent, preferably oil, more preferably mint oil.

In this way, an additional stability enhancement of the salicylate compound may be observed.

The composition may comprise up to 3 wt %, for example up to 2.5 wt %, up to 2 wt %, up to 1.5 wt %, up to 1 wt %, up to 0.5 wt %, up to 0.2 wt %, up to 0.18 wt % or up to 0.16 wt % flavouring agent, preferably oil, more preferably mint oil.

The concentration of flavouring agent, preferably oil, in the composition is suitably in the range from 0 to 3%, preferably 0.05 to 1%, more preferably 0.1 to 0.2%, particularly 0.12 to 0.18%, and especially 0.14 to 0.16% by weight based on the total weight of the composition.

The composition may also comprise an optional, additional natural or artificial sweetener or sweetening agent (in addition to saccharin). Suitable sweeteners are natural sugars which may be granulated or powdered, and include sucrose, fructose, dextrose, maltose, lactose, xylitol, polyols, and mixtures thereof.

In other embodiments, artificial sweeteners may be utilized in the composition. Suitable optional artificial sweeteners (in addition to saccharin) include, for example, cyclamates, sucralose, acesulfam-K, L-aspartyl-L-phenylalanine lower alkyl ester sweeteners (e.g. aspartame), L-aspartyl 1-D -alanine amides, L-aspartyl-D-serine amides, L-aspartyl-L-1-hydroxymethylalkaneamides, L-aspartyl-1-hydroxyethylalkaneamides, L-aspartyl-D-phenylglycine esters and amides.

The concentration of the optional, preferably artificial, sweetener (not including saccharin) in the composition is suitably in the range from 0 to 5%, preferably 0.4 to 2%, more preferably 0.7 to 1.3%, particularly 0.8 to 1.2%, and especially 0.9 to 1.1% by weight based on the total weight of the composition.

The composition according to the present invention may also contain an antioxidant. Suitable examples of antioxidants include a phenolic compound, a plant extract, or a sulphur-containing compound. The antioxidant may be ascorbic acid or a salt thereof, vitamin E, CoQIO, tocopherols, lipid soluble derivatives of more polar antioxidants such as ascorbyl fatty acid esters (e.g. ascorbyl palmitate), plant extracts (e.g. rosemary, sage and oregano oils, green tea extract), algal extracts, and synthetic antioxidants (e.g., butylated hydroxytoluene (BHT), tert-butylhydroquinone (TBHQ), butylated hydroxyanisole (BHA), ethoxyquin, alkyl gallates, hydroquinones, tocotrienols), and combinations thereof.

The concentration of the antioxidant in the composition is preferably in the range from 0 to 2%, more preferably 0.01 to 1.5%, particularly 0.1 to 1%, and especially 0.15 to 0.5% by weight based on the total weight of the composition.

The composition according to one embodiment of the invention comprises, consists essentially of, or consists of, aspirin, glycerin triacetate, saccharin and an optional flavouring agent.

The aspirin is preferably completely soluble in the composition and the composition is more preferably free of particulate material, as described above. The composition exhibits surprisingly improved stability to degradation. We have discovered that the flavouring agent, particularly mint oil, can also surprisingly contribute to the improved stability to degradation.

The composition according to the present invention is preferably stable, measured as described herein, suitably having a salicylate compound, e.g. aspirin degradation rate at 25° C. of less than 0.05%/day, preferably less than 0.04%/day, more preferably less than 0.03%/day, particularly less than 0.02%/day, and especially less than 0.015%/day.

The composition suitably has a salicylate compounds, e.g. aspirin degradation rate in mg per gram of composition per day at 25° C., measured as described herein, of less than 0.01 mg/g/day, preferably less than 0.007 mg/g/day, more preferably less than 0.006 mg/g/day, particularly less than 0.005 mg/g/day, and especially less than 0.004 mg/g/day.

The liquid composition described herein is particularly suitable for oral use as an alternative to normal aspirin tablets. One particular use is to orally administer to stroke or heart attack victims immediately after the attack, e.g. suitably within 12 hours, preferably within 8 hours, more preferably within 4 hours, particularly within 2 hours, and especially within 1 hour of the heart attack, e.g. in the ambulance on the way to hospital.

Formulations

Liquid compositions according to the present invention are preferably formulated as a pharmaceutical composition or medicament.

Thus, in some embodiment the liquid composition is a pharmaceutical composition or medicament. Methods of making a pharmaceutical composition or medicament comprising admixing the salicylate compound, glycerol derivative and saccharin compound are provided, which methods may optionally further comprise admixing together with one or more other pharmaceutically acceptable ingredients well known to those skilled in the art, e.g., carriers, adjuvants, excipients, etc. If formulated as discrete units (e.g., tablets/capsules, etc.), each unit contains a predetermined amount (dosage) of the active compound(s), i.e. the salicylate compound and/or glycerol derivative and/or saccharin compound.

The term "pharmaceutically acceptable" as used herein pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, adjuvant, excipient, etc. must also be "acceptable" in the sense of being compatible with the other ingredients of the formulation.

Suitable carriers, adjuvants, excipients, etc. can be found in standard pharmaceutical texts for example, *Remington's Pharmaceutical Sciences*. 18th edition. Mack Publishing Company, Easton, Pa., 1990; and *Handbook of Pharmaceutical Excipients,* 2nd edition, 1994.

Pharmaceutical formulations may be prepared by any methods well known in the art of pharmacy. Such methods include the step of bringing into association the active compound with a carrier which constitutes one or more accessory ingredients. In general, the formulations are prepared by uniformly and intimately bringing into association the active compound with carriers (e.g., liquid carriers, finely divided solid carrier, etc.), and then shaping the product, if necessary.

The formulation may be prepared to provide for rapid or slow release; immediate, delayed, timed, or sustained release; or a combination thereof.

Formulations may suitably be in the form of liquids, elixirs, syrups, mouthwashes, drops, capsules (including, e.g., gel capsules, hard and soft gelatin capsules), ampoules, sprays, mists, aerosols or vapours. Liquid formulations may be suitable for oral administration, e.g. in the form of a gel capsule filled with the liquid composition, or for intravenous or intraarterial administration, e.g. by injection. Liquid formulations may also be suitable for inhalation through the nose or mouth, e.g. when delivered as an aerosol or vapour.

Formulations suitable for inhalation administration, include, for example, nasal spray, nasal drops, or by aerosol administration by nebuliser. Formulations suitable for pulmonary administration (e.g., by inhalation or insufflation therapy) include those presented as an aerosol spray from a pressurised pack, with the use of a suitable propellant, such as dichlorodifluoromethane, trichlorofluoromethane, dichloro-tetrafluoroethane, carbon dioxide, or other suitable gases.

Formulations may suitably be provided as a patch, adhesive plaster, bandage, dressing, or the like which is impregnated with the liquid composition and optionally one or more other pharmaceutically acceptable ingredients, including, for example, penetration, permeation, and absorption enhancers.

Methods of Treatment

The liquid compositions described herein are useful in the treatment or prevention of diseases or disorders including, for example, those which are known to be treated with, or known to be treatable with salicylate compounds (e.g. aspirin).

In some aspects of the present invention the liquid composition is provided for use in a method of treatment of the human or animal body by therapy, for example, for use in a method of treatment of a disease or disorder.

Preferably, the beneficial therapeutic effects of the treatment outweigh any potentially harmful effects of the salicylate compound. For example, some salicylate compounds were thought to be associated with Reye's syndrome in children. In reality Reye's syndrome has only been observed rarely in children with Kawasaki Disease treated with high dose aspirin (Buck M L., '*Use of Aspirin in children with cardiac disease'*, *Pediatr Pharm* 2007; 13(1), incorporated herein by reference). There is in fact no convincing evidence linking the ingestion of Aspirin in children with the cause of Reye's syndrome. Most authorities now attribute Reye's syndrome to a viral aetiology. The implication of aspirin as a causative agent was due to the confounding factor that most of these children had a fever and were administered aspirin. Of course, the trained medical practitioner can assess such risk balanced against the benefits of the particular treatment. All children with Kawasaki disease are currently prescribed aspirin (often in high dose) as the risk: benefit ratio vastly favours benefit over risk.

In some aspects of the present invention a method of treatment is provided for the prevention or treatment of a disease or disorder, the method comprising administering to a patient in need of treatment a therapeutically effective amount of a liquid composition according to the present invention.

Another aspect of the present invention pertains to a method of treatment, for example, of a disorder (e.g., a disease) as described herein, comprising administering to a patient in need of treatment a therapeutically effective amount of a liquid composition, as described herein, preferably in the form of a pharmaceutical composition, and one or more (e.g., 1, 2, 3, 4) additional therapeutic agents, as described herein, preferably in the form of a pharmaceutical composition. In some embodiments the additional therapeutic agent may be administered in a separate composition, such administration being simultaneous, separate or sequential to the liquid composition of the present invention. The liquid composition of the present invention and additional therapeutic agent may be presented together in the form of a kit, optionally with instructions for their use. In other embodiments the additional therapeutic agent may be formulated together with the liquid composition of the present invention. In some embodiments where the disease being treated is a cancer an additional therapeutic agent may be a chemotherapeutic agent, e.g. temozolomide.

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, alleviation of symptoms of the condition, amelioration of the condition, and cure of the condition. Treatment as a prophylactic measure (i.e., prophylaxis) is also included. For example, use with patients who have not yet developed the condition, but who are at risk of developing the condition, is encompassed by the term "treatment."

For example, treatment of glioblastoma multiforme includes the prophylaxis of glioblastoma multiforme, reducing the incidence of glioblastoma multiforme, reducing the severity of glioblastoma multiforme, alleviating the symptoms of glioblastoma multiforme, etc.

The term "therapeutically-effective amount," as used herein, pertains to that amount of a compound, or a material, composition or dosage form comprising a compound, which is effective for producing some desired therapeutic effect, commensurate with a reasonable benefit/risk ratio, when administered in accordance with a desired treatment regimen.

Diseases or disorders to be treated or prevented may include any disease or disorder for which a salicylate compound, glycerol derivative or saccharin compound has a treatment effect, which may be a protective, preventative or prophylactic effect. Diseases or disorders to be treated may include fever, pain, inflammation, or swelling. Methods of treatment may also involve prevention of formation of blood clots, blood-thinning, or reduction of clot formation, prevention or reduction of heart attack, stroke or ischaemia, prevention or treatment of cancer.

In some embodiments a disease or disorder to be treated or prevented may be a cardiovascular disease, cerebrovascular disease or a cancer.

Salicylate compounds are known for the treatment or prevention of a range of cardiovascular and cerebrovascular disorders (e.g. see Hall, S L; Lorenc, T (1 Feb. 2010). "Secondary prevention of coronary artery disease". *American family physician* 81 (3): 289-96, incorporated herein by reference), for use in the treatment of prevention of cancer (e.g. see Fengming Lan et al., Antitumor effect of aspirin in glioblastoma cells by modulation of β-catenin/T-cell factor-mediated transcriptional activity. J Neurosurg 115:780-788, 2011, incorporated herein by reference), and as non-steroidal anti-inflammatory (NSAID) agents (e.g. see Morris et al., Effects of Low-Dose Aspirin on Acute Inflammatory Responses in Humans. The Journal of Immunology. 2009; 183:2089-2096, incorporated herein by reference).

Aspirin is a well-known salicylate drug widely used as an analgesic, antipyretic, anti-inflammatory and anti-platelet and therefore finds application in the treatment or prevention of pain, fever, and inflammation. Its anticoagulant action has made it popular in the treatment or prevention of cardiovascular diseases such as heart attack, stroke, and ischaemia.

The anti-cancer effect of aspirin was first reported in 1972 (Gasic G I, et al. Lancet. 1972; 2:932-937) and is well known. Recently, Fengming Lan et al; (supra) describe aspirin to be a potent antitumor agent, capable of inhibiting glioma cell proliferation and invasive ability and inducing apoptotic cell death. Low dose, long term aspirin use is proposed as having a future role in preventing glioma or as an adjuvant therapeutic agent in the treatment of glioma (Matthew W. Brown., Characterisation of the effects of chronic aspirin treatment on the viability and proliferation of stage 4 glioblastoma cells. Diffusion: the UCLan Journal of Undergraduate Research Volume 6 Issue 2 Dec. 2013, incorporated herein by reference).

See also the additional references cited in the background section, above.

Glycerin triacetate freely crosses the blood-brain barrier and has been shown to be effective as an adjuvant in the chemotherapeutic treatment of glioma slowing the growth of glioma stem cells in culture but not affecting normal glial cells or neural stem cells (e.g. see Tsen et al., Triacetin-based acetate supplementation as a chemotherapeutic adjuvant therapy in glioma. Int J Cancer. 2014 Mar. 15; 134(6):1300-1310; and Long et al., 'Acetate Supplementation Induces Growth Arrest of NG2/PDGFRa-Positive Oligodendro- glioma-Derived Tumor-Initiating Cells', PLoS One, 2013, e80714, both incorporated herein by reference). Glycerin triacetate enhanced the efficacy of temozolomide against glioma when the two agents were administered in combination. The inventors expected glycerin triacetate to provide a similar effect in salicylate compound, e.g. aspirin, therapy, to enhance the delivery of the salicylate compound across the blood-brain barrier when the two are administered in combination, as in the present liquid compositions. A synergistic effect may thus be observed for the salicylate compound treatment of cerebrovascular disorders such as stroke or dementia with the present compositions. A synergistic effect may also be observed for the combination of aspirin, saccharin and glycerin triacetate. Furthermore, since glycerin triacetate transports aspirin across the blood-brain barrier, the efficacy of the treatment will increase.

Given that both glycerin triacetate and aspirin have been shown to have chemotherapeutic properties, the liquid compositions of the invention containing these compounds provide a highly efficacious combination therapy against cancer, in particular brain cancer, especially primary brain cancer and gliomas such as glioblastoma multiforme. The stable and fully solubilised nature of the compositions means that such combination therapy can be very easily provided. Additionally, since Tsen et al. (supra) demonstrated that glycerin triacetate enhances temozolomide chemotherapeutic efficacy, a similar effect is expected to be observed in the compositions of the invention, with an enhancement in the chemotherapeutic effect of aspirin being provided by glycerin triacetate. The present compositions may therefore provide aspirin as a chemotherapeutic agent with enhanced efficacy when compared with the administration of aspirin alone, especially for the treatment of glioma. The aspirin is stable and solubilised in the compositions and is therefore much more easily administered with fewer side-effects.

Saccharin based compounds have been reported to bind to and deactivate carbonic anhydrase IX which is found in several aggressive cancers. Saccharin based compounds have recently been proposed as a new class of anti-cancer agent (Mahon et al., Saccharin: a lead compound for structure-based drug design of carbonic anhydrase IX inhibitors. Bioorg Med Chem 2015 Feb. 15; 23(4):849-54, incorporated herein by reference). Proescholdt et al. ('Function of carbonic anhydrase IX in glioblastoma multiforme', Neuro Oncol, 2012, Vol. 14, pp. 1357-1366) suggest that inhibition of carbonic anhydrase IX is a potential metabolic target for the treatment of glioblastoma patients.

Cardiovascular diseases or disorders that may be treated or prevented include angina pectoris; heart failure (HF); left or right ventricular failure; pulmonary heart disease; ischaemic heart disease (IHD); cardiomyopathy; cardiac dysrhythmia; stenosis of a heart valve; hypertrophic cardiomyopathy (HCM); and coronary heart disease.

In some embodiments, the treatment is treatment of angina pectoris (also known as angina), for example, angina pectoris caused by coronary heart disease; angina pectoris caused by ischaemia; severe angina pectoris; or unresponsive or refractory angina pectoris.

In some embodiments, the treatment is treatment of heart failure (HF), for example, heart failure caused by ischaemia; congestive heart failure; chronic heart failure; moderate heart failure; systolic heart failure; diastolic heart failure; or diastolic heart failure with left ventricular injury.

In some embodiments, the treatment is treatment of left or right ventricular failure, for example, of various aetiologies.

In some embodiments, the treatment is treatment of pulmonary heart disease, for example, pulmonary heart disease caused by pulmonary hypertension; pulmonary heart disease caused by chronic obstructive lung disease; or pulmonary heart disease caused by emphysema.

In some embodiments, the treatment is treatment of ischaemic heart disease (IHD), for example, ischaemic heart disease caused by coronary heart disease; ischaemic heart disease caused by obstruction of the coronary artery; ischaemic heart disease caused by spasm of the coronary artery; severe ischaemic heart disease (e.g., in a patient awaiting coronary revascularisation); or refractory ischaemic heart disease (e.g., in a patient with ischaemic symptoms refractory to other therapeutic measures).

In some embodiments, the treatment is treatment of cardiomyopathy, including, for example, cardiomyopathy due to ischaemic heart disease; or cardiomyopathy due to hypertension.

In some embodiments, the treatment is treatment of cardiac dysrhythmia (also known as cardiac arrhythmia or irregular heartbeat), for example, cardiac dysrhythmia caused by ischaemia.

In some embodiments, the treatment is treatment of stenosis of a heart valve, for example, aortic stenosis, for example, inoperable aortic stenosis.

In some embodiments, the treatment is treatment of hypertrophic cardiomyopathy (HCM), for example, symptomatic non-obstructive hypertrophic cardiomyopathy.

In some embodiments, the treatment is treatment of coronary heart disease.

In some embodiments, the treatment is of paediatric cardiovascular disease, for example Kawasaki disease.

In some embodiments, the treatment is of congenital heart disease.

Cerebrovascular disorders or disorders that may be treated or prevented include stroke (e.g. thrombotic or embolic stroke), cerebral ischeamia, brain ischaemia, transient ischaemic attack (TIA) and vascular dementia.

In some embodiments, the treatment is treatment of stroke (e.g. thrombotic or embolic stroke), transient ischaemic attack (TIA) or vascular dementia.

In some embodiments, the treatment is treatment of stroke (e.g. thrombotic or embolic stroke), cerebral ischemia or brain ischaemia.

In some embodiments, the treatment is treatment of vascular dementia.

A cancer may be any unwanted cell proliferation (or any disease manifesting itself by unwanted cell proliferation), neoplasm or tumor or increased risk of or predisposition to the unwanted cell proliferation, neoplasm or tumor. The cancer may be benign or malignant and may be primary or secondary (metastatic). A neoplasm or tumor may be any abnormal growth or proliferation of cells and may be located in any tissue. Examples of tissues include the adrenal gland (cortex and/or medulla), anus, appendix, bladder, blood, bone, bone marrow, brain, breast, caecum (and/or any part of the large intestine), central nervous system (including or excluding the brain) cerebellum, duodenum and/or any other part of the small intestine, epithelial cells, gallbladder, oesophagus, glial cells, heart, kidney, lacrimal gland, larynx, liver, lung, lymph, lymph node, lymphoblast, maxilla, mediastinum, mesentery, myometrium, nasopharynx, omentum, oral cavity, ovary, pancreas, parotid gland, peripheral nervous system, peritoneum, pleura, prostate, salivary gland, skin, soft tissues, spleen, stomach, testis, thymus, thyroid gland, tongue, tonsil, trachea, uterus (endo- and myometrium), cervix uteri, vulva, blood cells (leukoid and/or myeloid lines).

Cancers that may be treated or prevented include acute myeloid leukaemia; adrenal gland cancer; biliary tract cancer; bladder cancer; bone cancer; bowel cancer; brain cancer; breast cancer; colon cancer; colorectal cancer; endometrial cancer; gastrointestinal cancer; genito-urinary cancer; glioma; glioblastoma; gynaecological cancer; head cancer; Hodgkin's disease; Kaposi's sarcoma; kidney cancer; large bowel cancer; leukaemia; liver cancer; lung cancer; lymphoma; lymphocytic leukaemia (lymphoblastic leukaemia); malignant melanoma; mediastinum cancer; melanoma; myeloma; myelogenous leukaemia (myeloid leukaemia); nasopharyngeal cancer; neck cancer; nervous system cancer; non-Hodgkin's lymphoma; non-small cell lung cancer;

oesophagus cancer; osteosarcoma; ovarian cancer; pancreatic cancer; prostate cancer; rectal cancer; renal cell carcinoma; sarcoma; skin cancer; small bowel cancer; small cell lung cancer; soft tissue sarcoma; squamous cancer; stomach cancer; testicular cancer; and thyroid cancer.

In some embodiments, the treatment is treatment of cancer of the gastro-intestinal tract.

Tumors to be treated may be nervous or non-nervous system tumors. Nervous system tumors may originate either in the central or peripheral nervous system, e.g. glioma, gliobastoma multiforme, medulloblastoma, meningioma, neurofibroma, ependymoma, Schwannoma, neurofibrosarcoma, astrocytoma and oligodendroglioma. Tumors may be of the central nervous system, e.g. brain tumors, and may be primary or secondary (metastatic). Non-nervous system cancers/tumors may originate in any other non-nervous tissue, examples include melanoma, mesothelioma, lymphoma, myeloma, leukemia, Non-Hodgkin's lymphoma (NHL), Hodgkin's lymphoma, chronic myelogenous leukemia (CML), acute myeloid leukemia (AML), myelodysplastic syndrome (MDS), cutaneous T-cell lymphoma (CTCL), chronic lymphocytic leukemia (CLL), hepatoma, epidermoid carcinoma, prostate carcinoma, breast cancer, lung cancer, colon cancer, ovarian cancer, pancreatic cancer, thymic carcinoma, NSCLC, haematologic cancer and sarcoma.

In some embodiments, the treatment is of cancer of the central nervous system, e.g. brain. The cancer to be treated may be a primary cancer or tumor. In some preferred embodiments the cancer is a glioma, glioblastoma multiforme, high grade glioma, diffuse intrinsic pontine glioma, medulloblastoma, meningioma, neurofibroma, ependymoma, Schwannoma, neurofibrosarcoma, astrocytoma or oligodendroglioma.

Subjects

The subject to be treated may be any animal or human. The subject is preferably mammalian, more preferably human. The subject may be a non-human mammal, but is more preferably human. The subject may be male or female. The subject may be a patient. A subject may have been diagnosed with a cardiovascular disease, cerebrovascular disease or a cancer, or be suspected of having a cardiovascular disease, cerebrovascular disease or a cancer. In some embodiments the subject may be an adult, i.e. of the age 18 or over. In some embodiments a subject may be a child, e.g. a subject under the age of 18, under the age of 16, or under the age of 12.

Routes of Administration

The liquid pharmaceutical composition comprising the salicylate compound may be administered to a subject by any convenient route of administration, whether systemically/peripherally or topically (i.e., at the site of desired action).

Routes of administration include, but are not limited to, oral (e.g., by ingestion); buccal; sublingual; transdermal (including, e.g., by a patch, plaster, etc.); transmucosal (including, e.g., by a patch, plaster, etc.); intranasal (e.g., by nasal spray, drops or from an atomiser or dry powder delivery device); ocular (e.g., by eyedrops); pulmonary (e.g., by inhalation or insufflation therapy using, e.g., an aerosol or vapour, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

In one preferred embodiment, the route of administration is oral (e.g., by ingestion).

In one preferred embodiment, the route of administration is parenteral (e.g., by injection).

In one preferred embodiment, the route of administration is rectal.

In one preferred embodiment, the route of administration is nasogastric.

In one preferred embodiment, the route of administration is pulmonary (e.g. by inhalation or insufflation therapy using e.g. an aerosol or vapour through e.g. the mouth or nose).

The invention provides a composition which is easily administered e.g. by the patient themselves orally or by inhalation or insufflation. Furthermore the liquid composition may be more easily administered to a patient in need thereof who may be unable to accept a solid formulation.

Dosage

It will be appreciated by one of skill in the art that appropriate dosages of the compositions comprising the salicylate compound can vary from patient to patient. Determining the optimal dosage will generally involve the balancing of the level of therapeutic benefit against any risk or deleterious side effects. The selected dosage level will depend on a variety of factors including, but not limited to, the activity of the particular salicylate compound, the route of administration, the time of administration, the rate of excretion of the salicylate compound, the duration of the treatment, other drugs, compounds, and/or materials used in combination, the severity of the condition, and the species, sex, age, weight, condition, general health, and prior medical history of the patient. The amount of salicylate compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of aspirin for the treatment of the disorders described herein is in the range of about 1-30 mg per kilogram body weight of the subject per day. Where the compound is a salt, an ester, an amide, a prodrug, or the like, the amount administered is calculated on the basis of the parent compound and so the actual weight to be used is increased proportionately.

For the compositions according to the invention an improved bioavailability and absorption of the salicylate compound (e.g. aspirin) may be observed. Therefore, a lower dose that necessary for standard compositions may be expected to achieve the same level of therapeutic effect.

For the treatment or prevention of cardiovascular conditions, a suitable dose is typically about 75 mg or less, e.g. one of about 10 to 75 mg, 10 to 65 mg, 10 to 55 mg, 10 to 45 mg, or 10 to 20 mg. Formulations may be of any kind, including for oral administration. Administration of the dose may be once daily.

For the treatment of pain, e.g. headache, a suitable dose is typically in the range 300 to 600 mg, e.g. one of about 300 mg, about 325 mg, about 350 mg, about 400 mg, about 450 mg, about 500 mg, about 550 mg or about 600 mg. Formulations may be of any kind, including for oral administration.

For the treatment of cancer, a suitable dose is typically about 4 g or less, based on the maximum tolerated dose of aspirin for human patients being about 4 g. For example, each dose may be one of about 1 g, 1.5 g, 2 g, 2.5 g, 3 g or 4 g. In some preferred embodiments, the dose may be in the range 1.5 to 3 g, or 2 to 2.5 g or 2 to 2.4 g. In some preferred embodiments, the dose may be one of about 2 g, 2.1 g, 2.2 g, 2.3 g, 2.4 g or 2.5 g. Formulations may be of any kind, including for oral administration or intravenous infusion. In preferred embodiments for the treatment of cancer, formulation may be for intravenous infusion.

Packaging and Kits

One aspect of the invention pertains to a kit comprising (a) a liquid composition as described herein, e.g., preferably provided in a suitable container and/or with suitable packaging; and (b) instructions for use, e.g., written instructions on how to administer the composition.

The kit may have at least one container having a predetermined quantity of the liquid composition, e.g. predetermined dose or volume.

In one embodiment, the kit further comprises one or more (e.g., 1, 2, 3, 4) additional therapeutic agents, as described herein.

The written instructions may also include a list of indications for which the active ingredient is a suitable treatment.

In some embodiments the kit may also contain apparatus suitable to administer one or more doses of the liquid composition, such apparatus preferably being provided in sterile form.

In some embodiments, the kit may include packaging manufacturers by the Blow-Fill-Seal (BFS) method.

In some embodiments a method of manufacturing a kit according to the present invention may include the step of preventing water infiltration into the composition.

The liquid composition may be packaged into bottles for dispensing with a spoon or a pipette. Alternatively the composition may be packaged into a syringe, vial, or in a sachet or 'stick shot', such as a laminate 'stick shot'. The composition is suitably packaged in individual 5 to 10 ml, preferably 5 ml servings.

The syringe may be a pre-filled syringe.

The liquid composition may also be incorporated in liquid gel capsules, e.g. in a dose of 37.5 mg per capsule or in a dose of one of 10-50 mg per capsule, 20-40 mg per capsule, or 30-40 mg per capsule. This preparation would be particularly applicable to long term cardiovascular, cerebrovascular and cancer prevention uses.

Methods according to the present invention may be performed, or products may be present, in vitro, ex vivo, or in vivo. The term "in vitro" is intended to encompass experiments with materials, biological substances, cells and/or tissues in laboratory conditions or in culture whereas the term "in vivo" is intended to encompass experiments and procedures with intact multi-cellular organisms. "Ex vivo" refers to something present or taking place outside an organism, e.g. outside the human or animal body, which may be on tissue (e.g. whole organs) or cells taken from the organism.

All of the features described herein may be combined with any of the above aspects of the invention, in any combination. In addition, any upper or lower quantity or range limit used herein may be independently combined.

The invention includes the combination of the aspects and preferred features described except where such a combination is clearly impermissible or expressly avoided.

The section headings used herein are for organizational purposes only and are not to be construed as limiting the subject matter described.

Aspects and embodiments of the present invention will now be illustrated, by way of example, with reference to the accompanying figures. Further aspects and embodiments will be apparent to those skilled in the art. All documents mentioned in this text are incorporated herein by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

BRIEF DESCRIPTION OF THE FIGURES

Embodiments and experiments illustrating the principles of the invention will now be discussed with reference to the accompanying figures in which.

Figure 1:
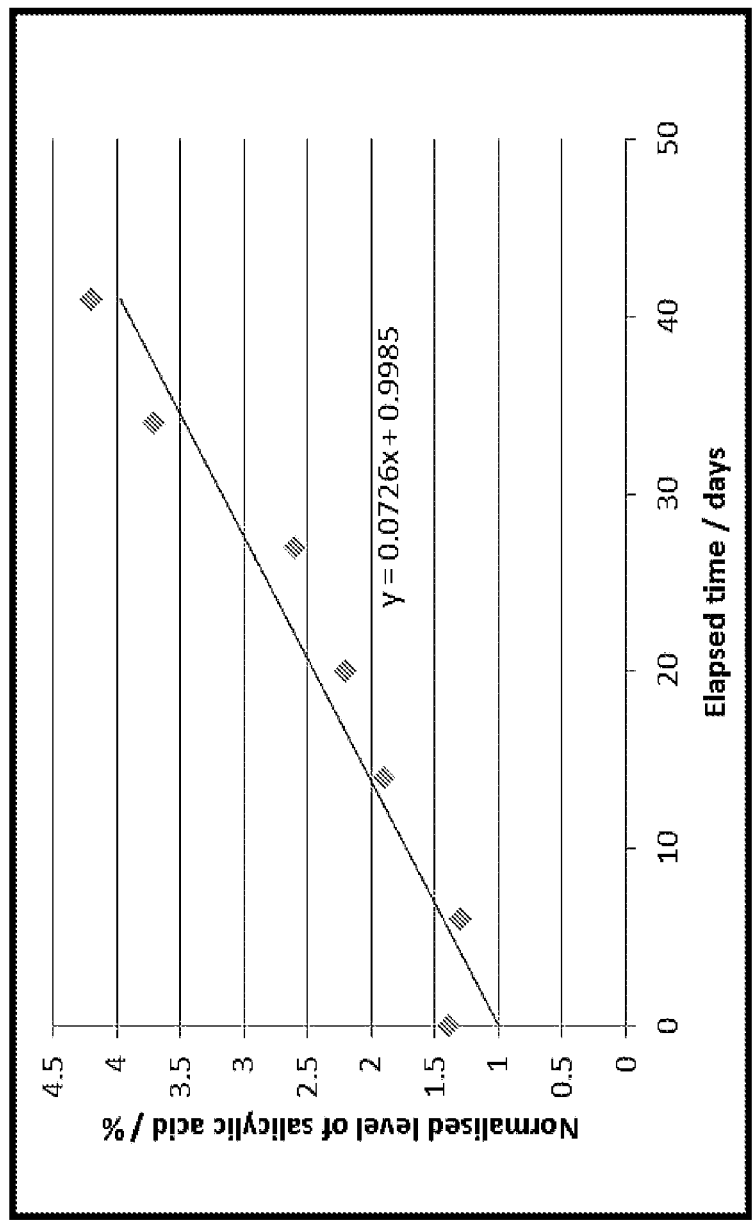
FIG. 1 is a plot of the normalized % of salicylic acid present in a test composition against the number of days elapsed since preparation of the composition, for a composition of 90 wt % glycerol+20EO and 10 wt % aspirin. The test was conducted at 25° C.

In this specification the following test method was used:
Aspirin Stability

Aspirin undergoes hydrolysis to salicylic acid and acetic acid. The aspirin and salicylic acid concentrations in the sample composition were determined for a minimum period of at least 200 days, preferably up to a maximum of 300 days. The composition was stored in a sealed glass vial in an oven at 25° C., and the concentration of aspirin and salicylic acid measured weekly. The glass vial was opened, a sample removed for testing every week and the glass vial resealed after purging with nitrogen. High performance liquid chromatography with UV detection was used. The conditions were as follows:

Mobile phase: 40% of 1% acetic acid in water, 60% methanol.
Column: Agilent Zorbax Eclipse XBD-C18. 4.6 mm×150 mm with 5 micron particle size.
Column heater: 25° C.
Sample concentration: 0.02 g made to 10 ml with mobile phase.
Injection volume: 40 microlitre.
Flow rate: 1 ml minute.
Detection: UV at 280 nm.

The stability of the aspirin in the composition is defined as the aspirin degradation rate which was calculated as (i) the average % aspirin degradation (based on the original aspirin concentration) per day, and (ii) the average % aspirin degradation (based on the original aspirin concentration) per gram of composition per day.

The invention is illustrated by the following non-limiting examples.

EXAMPLES

Example 1

Food grade glycerin triacetate (ex Sigma Aldrich) was mixed with ethanol 40% w/v and passed through a fixed bed of activated earth. The solvent was then removed using vacuum distillation followed by steam distillation to levels below 1 ppm of ethanol in the glycerin triacetate.

Example 2

A composition was prepared by mixing 2.5 wt % aspirin (ex Sigma Aldrich), 96.5 wt % glycerin triacetate (produced in Example 1), and 1 wt % saccharin (ex Sigma Aldrich). The components were mixed in the appropriate ratios and sonicated to achieve complete solution. Microscopy showed that the solution was free of any particulate material. The aspirin stability in the composition was measured weekly as described above. The aspirin degradation after 277 days was 6.9% of the original amount present, which is equivalent to a degradation rate of 0.025%/day.

Example 3

The procedure of Example 2 was repeated except that the composition additionally contained 0.15 wt % of spearmint oil (ex Quinessence) (and correspondingly 0.15 wt % less of glycerin triacetate, i.e. 96.35 wt %). The aspirin degradation after 246 days was 5.7% of the original amount present, which is equivalent to a degradation rate of 0.023%/day.

Example 4

A composition was prepared by mixing 2.5 wt % aspirin (ex Sigma Aldrich), 96.5 wt % glycerin triacetate (produced in Example 1), and 1 wt % saccharin (ex Sigma Aldrich). The components were mixed in the appropriate ratios and sonicated to achieve complete solution. Microscopy showed that the solution was free of any particulate material. The aspirin stability in the composition was measured weekly as described above.

The "normalised % salicylic acid" was calculated by finding the % salicylic acid in the composition, as a percentage of the total % salicylic acid and aspirin in the composition, according to the formula Normalised % salicylic acid=(% salicylic acid)/(% aspirin+% salicylic acid)

Figure 3:
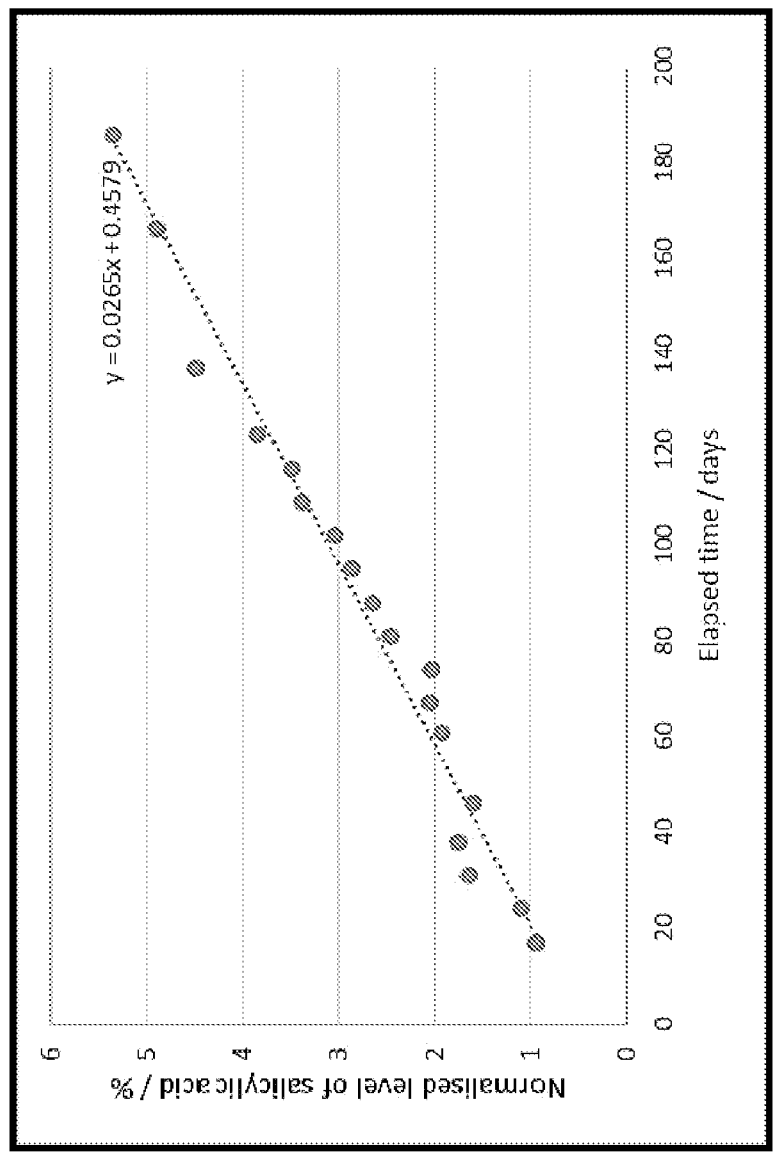
FIG. 3 is a plot of the normalized % of salicylic acid present in a test composition against the number of days elapsed since preparation of the composition, for a composition of 96.5 wt % glycerin triacetate, 2.5 wt % aspirin and 1 wt % saccharin. The test was conducted at 25° C.
Figure 4A:
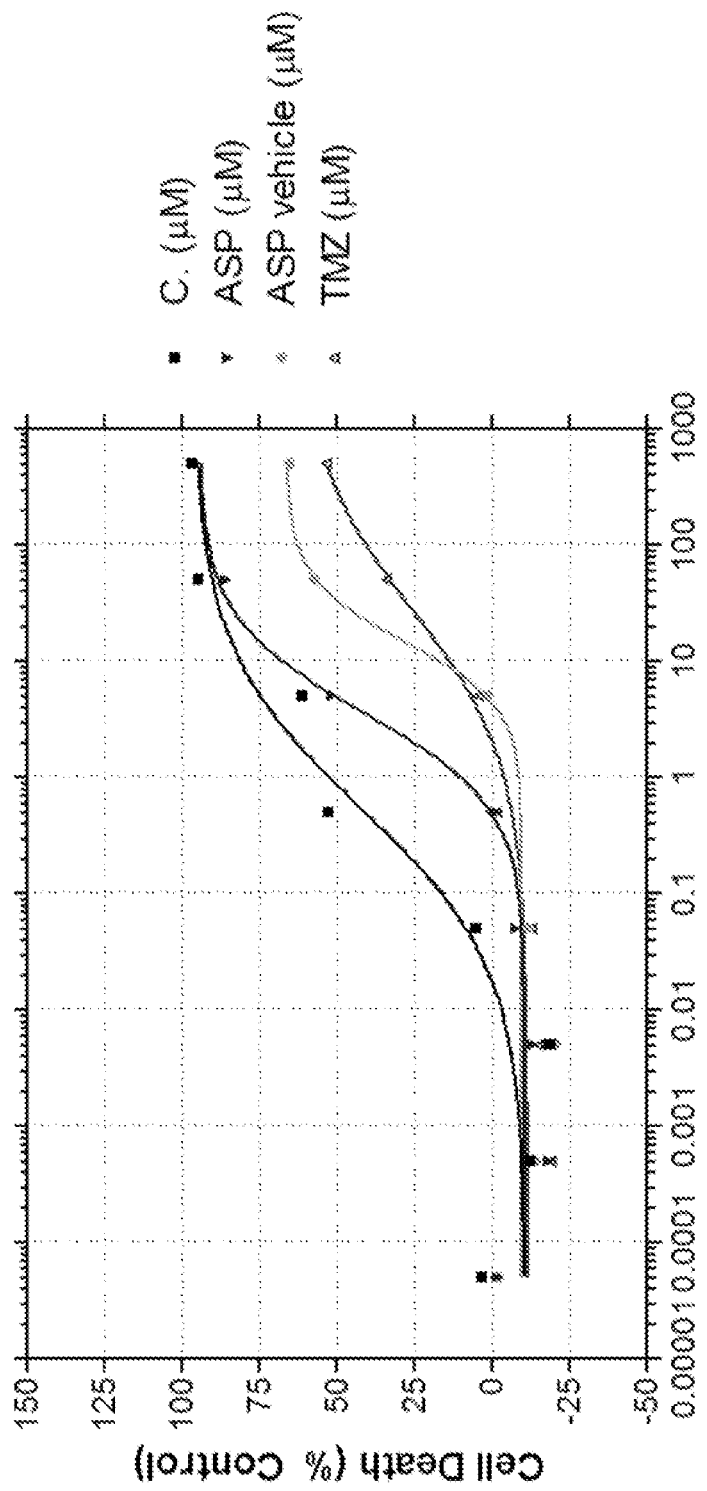
FIGS. 4A to 4E. Charts showing percentage cell death with varying concentration of drug (liquid aspirin (ASP); triacetin alone (ASP vehicle); temozolomide alone (TMZ)) in ex vivo patient glioblastoma cell lines (A) SEBTA 023, (B) SEBTA 003, (C) UP 029, (D) KNS42, (E) SNF188. Studies were conducted at 96 hours post-drug treatment and show the average (+/−StDev) of three experiments conducted in triplicate. Due to solubility issues, aspirin alone was not included in this study due to an inability to treat at comparable concentrations.
Figure 4B:
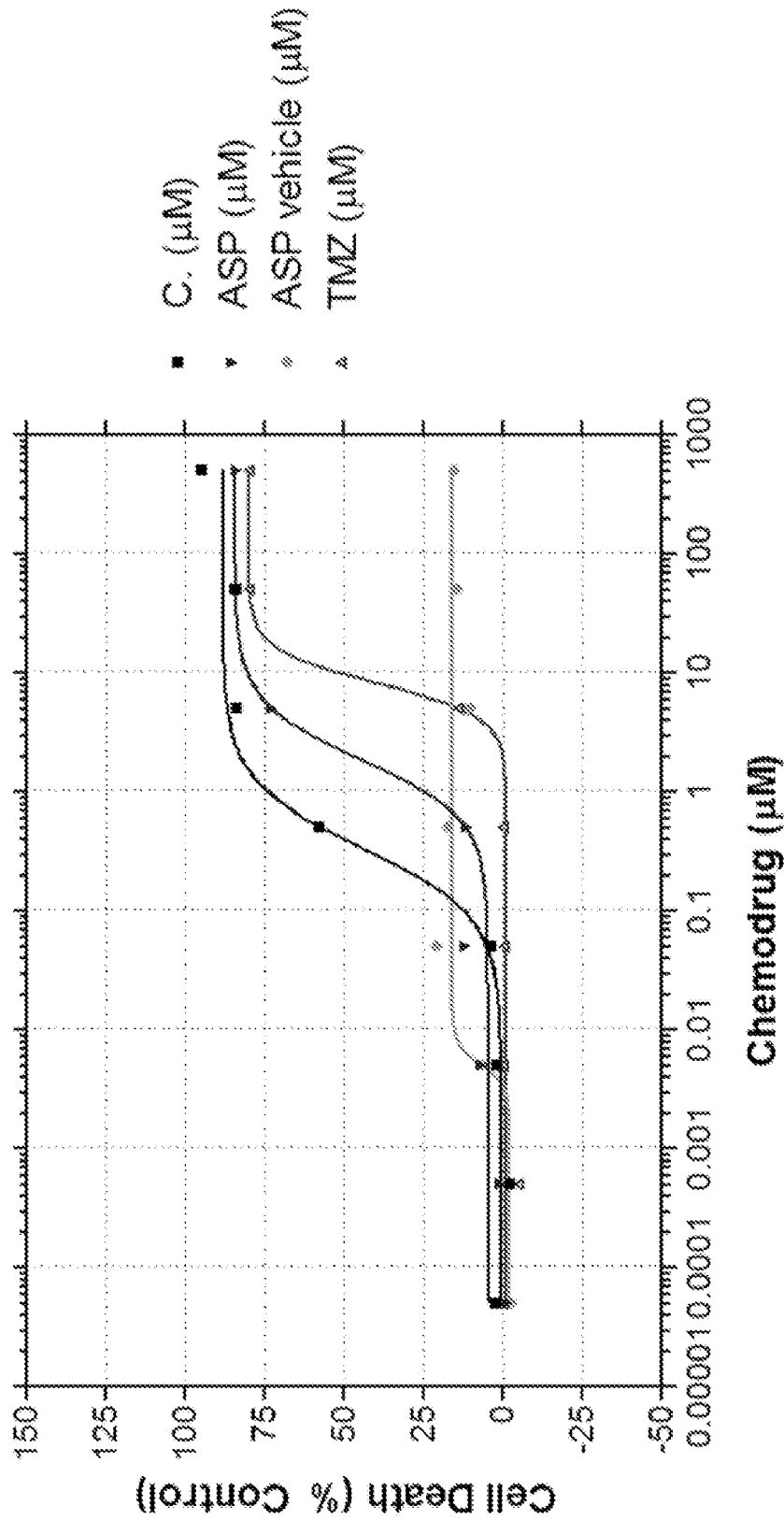
Figure 4C:
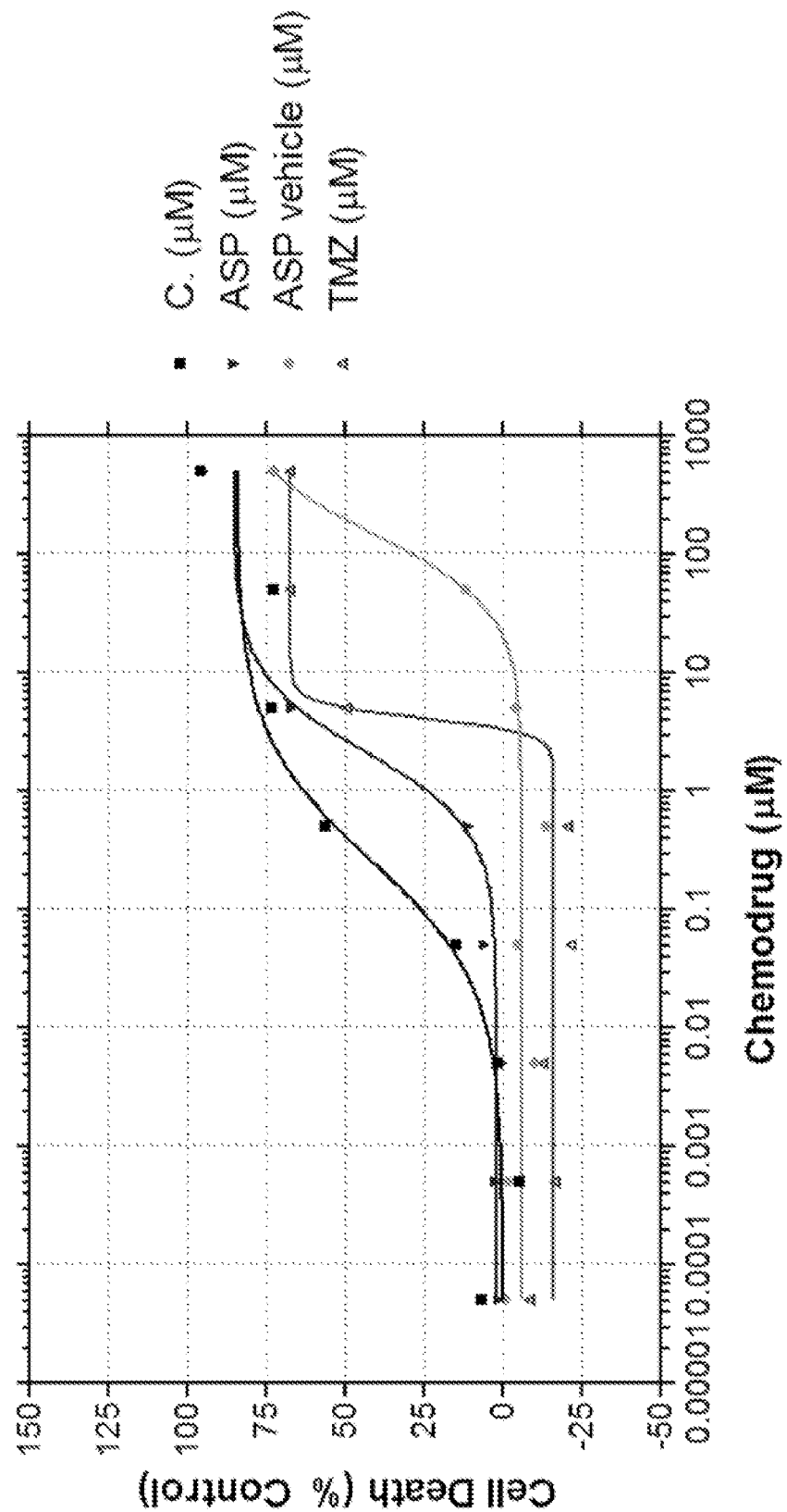
Figure 4D:
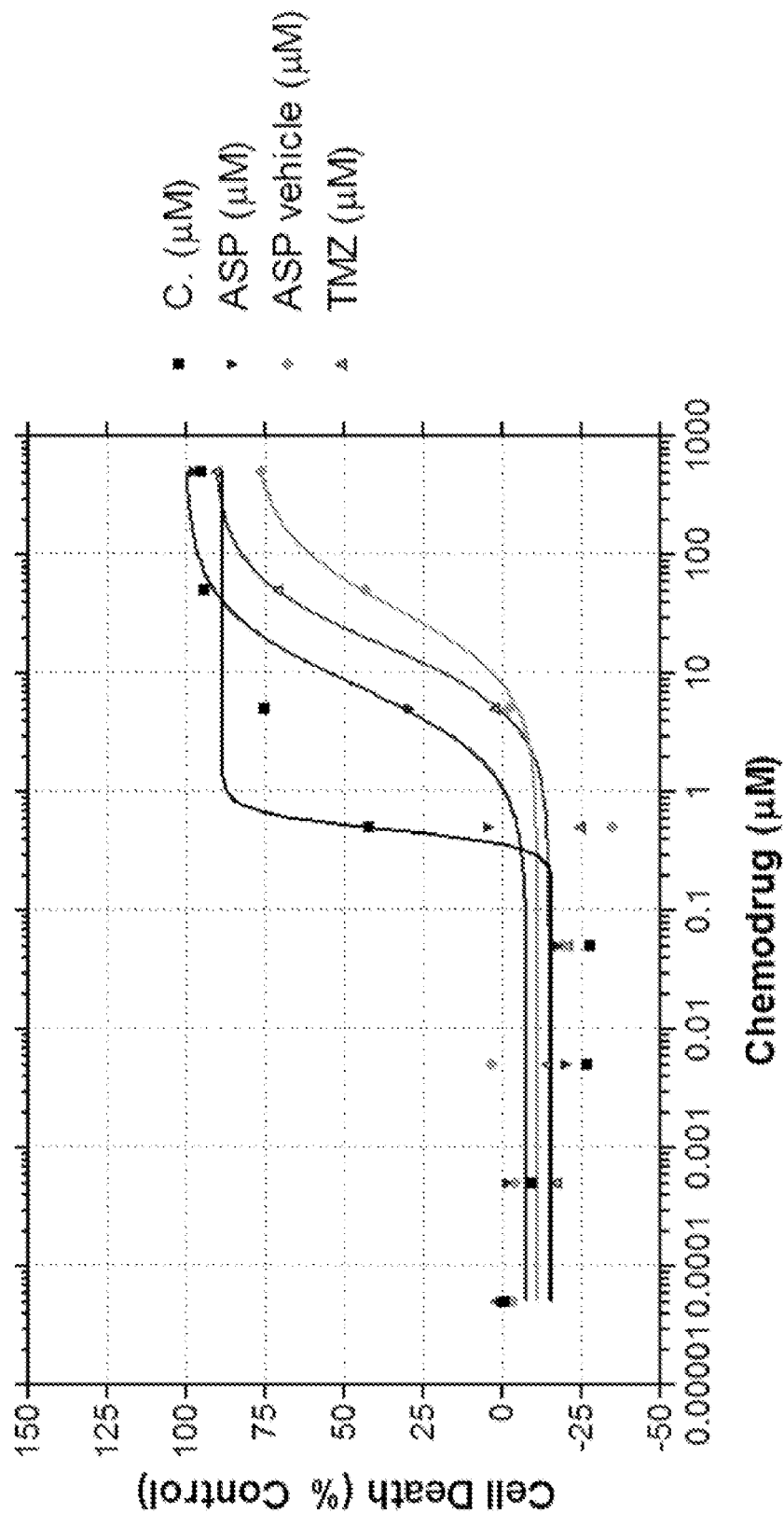
Figure 4E:
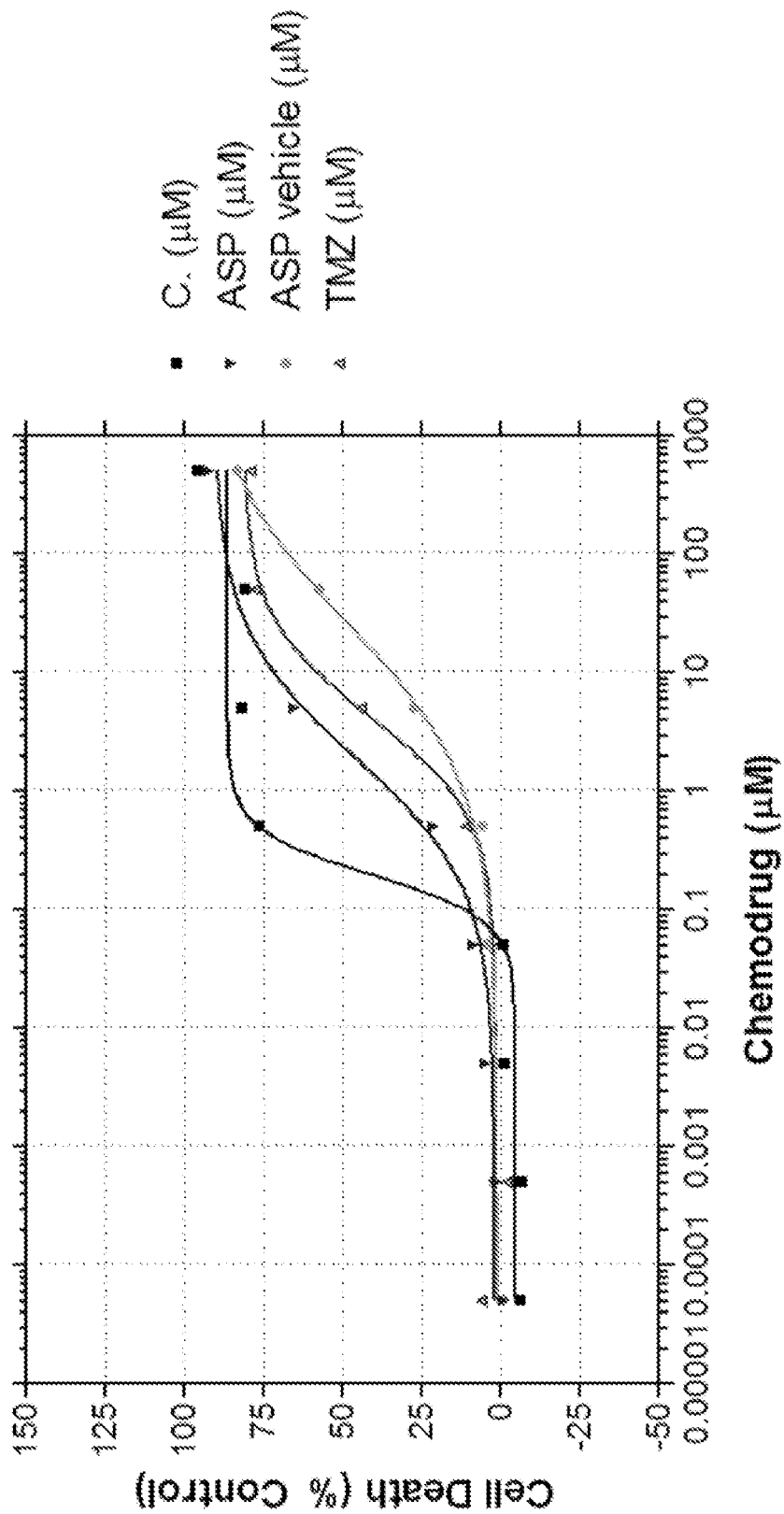
Figure 5:
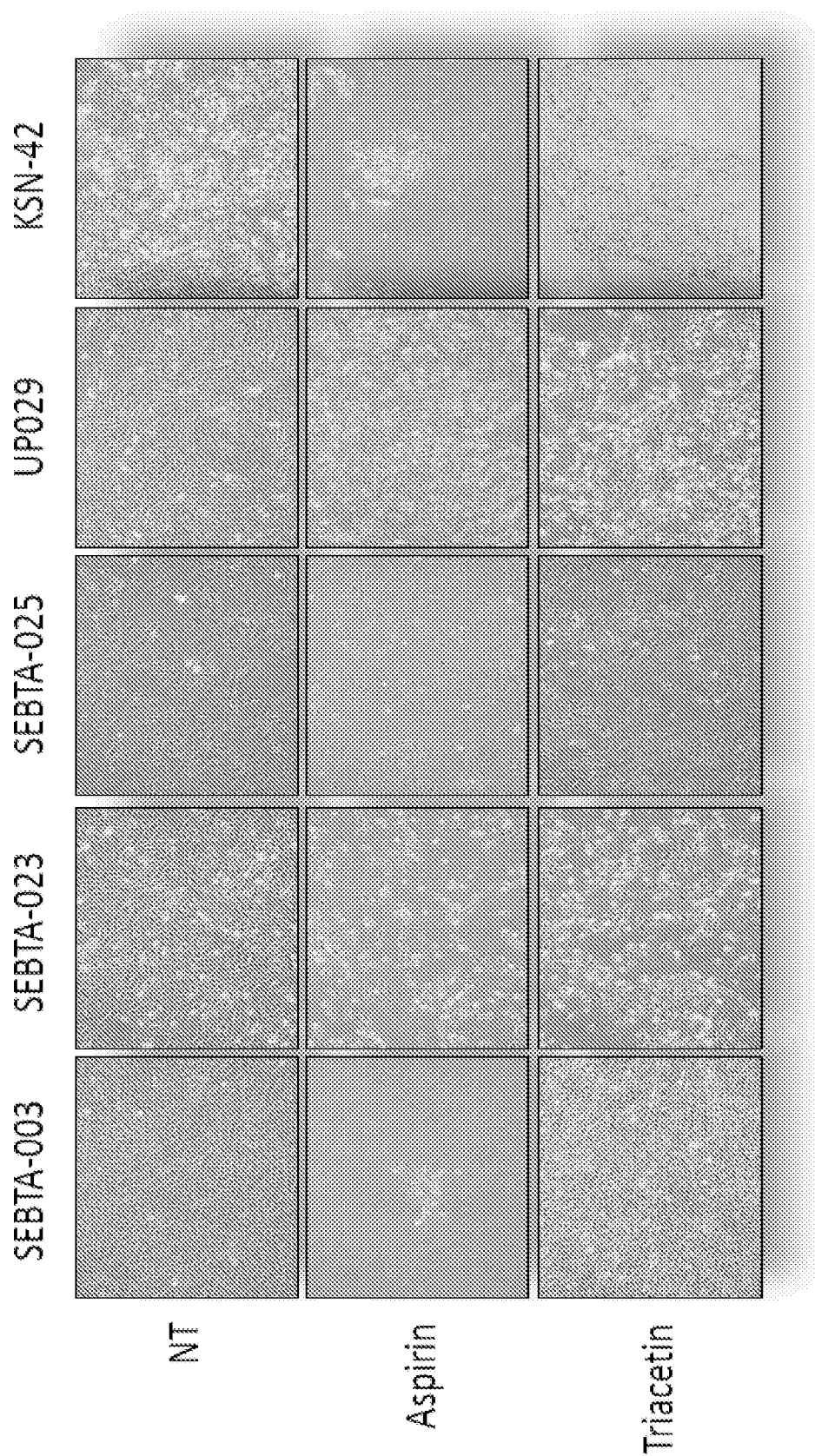
FIG. 5. Representative microscopy images of treated ex vivo biopsy-derived cell lines. Images show non-treated (NT), liquid aspirin ("aspirin") and triacetin only treatment. Contrast differences are the result of cell media pH changes following drug treatment and not due to cell confluence variation.

The results are shown in Table 1 below, and in FIG. 3.

TABLE 1

| Day | Normalised % salicylic acid |
|---|---|
| 17 | 0.941483 |
| 24 | 1.108112 |
| 31 | 1.644392 |
| 38 | 1.763869 |
| 46 | 1.610604 |
| 61 | 1.932933 |
| 67 | 2.056293 |
| 74 | 2.043556 |
| 81 | 2.468435 |
| 88 | 2.647186 |
| 95 | 2.868206 |

TABLE 1-continued

| Day | Normalised % salicylic acid |
|---|---|
| 102 | 3.043231 |
| 109 | 3.394404 |
| 116 | 3.499079 |
| 123 | 3.856439 |
| 137 | 4.496758 |
| 166 | 4.909486 |
| 186 | 5.350264 |

The observed 5.35% degradation after 186 days is equivalent to a degradation rate of 0.0288%/day.

Extrapolating from these results, the predicted shelf life limit (the point in time after initial preparation at which the normalised % salicylic acid reaches 10%) is 360 days.

Example 5

Compositions of aspirin with glycerin triacetate and saccharin were prepared according to the method of Example 2. Five compositions were prepared, with aspirin concentrations of 2.5 wt %, 3.0 wt %, 3.5 wt %, 4.0 wt % and 4.5 wt % respectively. Each composition also contained 1 wt % saccharin and the balance glycerin triacetate.

The compositions were tested for solubility at different temperatures. Compositions were observed to determine whether the aspirin had fully dissolved to provide a clear solution and whether the solution remained clear.

The results are shown in Table 2 below:

TABLE 2

| Aspirin concentration | Stable solubility at temperature | | | | |
|---|---|---|---|---|---|
| (wt %) | 25° C. | 20° C. | 15° C. | 10° C. | 4° C. |
| 2.5 | YES | YES | YES | YES | YES |
| 3.0 | YES | YES | YES | YES | NO |
| 3.5 | YES | YES | YES | YES | NO |
| 4.0 | YES | NO | NO | NO | NO |

The results demonstrate stable solubilisation of aspirin in the composition of the present invention at 4 wt % concentration at 25° C. At a concentration of 2.5 wt % the aspirin was stably solubilised at temperatures down to 4° C.

The compositions of the invention are therefore particularly suitable for use in the treatment of cardiovascular and cerebrovascular disorders and cancer, where low doses of aspirin over extended periods are required.

For example, at 2.5 wt % aspirin, a 2 mL dose in a gel capsule would provide around 50 mg aspirin. A 1 mL dose would provide around 25 mg aspirin.

Comparative Example 1

A composition was prepared by mixing 10 wt % aspirin (ex Sigma Aldrich) and 90 wt % glycerol+20EO (glycerol ethoxylated with 20 mol equivalents of ethylene oxide). The components were mixed in the appropriate ratios and sonicated to achieve complete solution. Microscopy showed that the solution was free of any particulate material. The aspirin stability in the composition was measured weekly as described above.

The results are shown in Table 3 below, and in FIG. 1.

TABLE 3

| Day | Normalised % salicylic acid |
| --- | --- |
| 0 | 1.4 |
| 6 | 1.3 |
| 14 | 1.9 |
| 20 | 2.2 |
| 27 | 2.6 |
| 34 | 3.7 |
| 41 | 4.2 |

The average degradation rate is 0.102%/day. Extrapolation from these results gives a predicted shelf life of 124 days.

Comparative Example 2

A composition was prepared by mixing 10 wt % aspirin (ex Sigma Aldrich), 1% saccharin (ex Sigma Aldrich) and 89 wt % glycerol+20EO. The components were mixed in the appropriate ratios and sonicated to achieve complete solution. Microscopy showed that the solution was free of any particulate material. The aspirin stability in the composition was measured weekly as described above.

Figure 2:
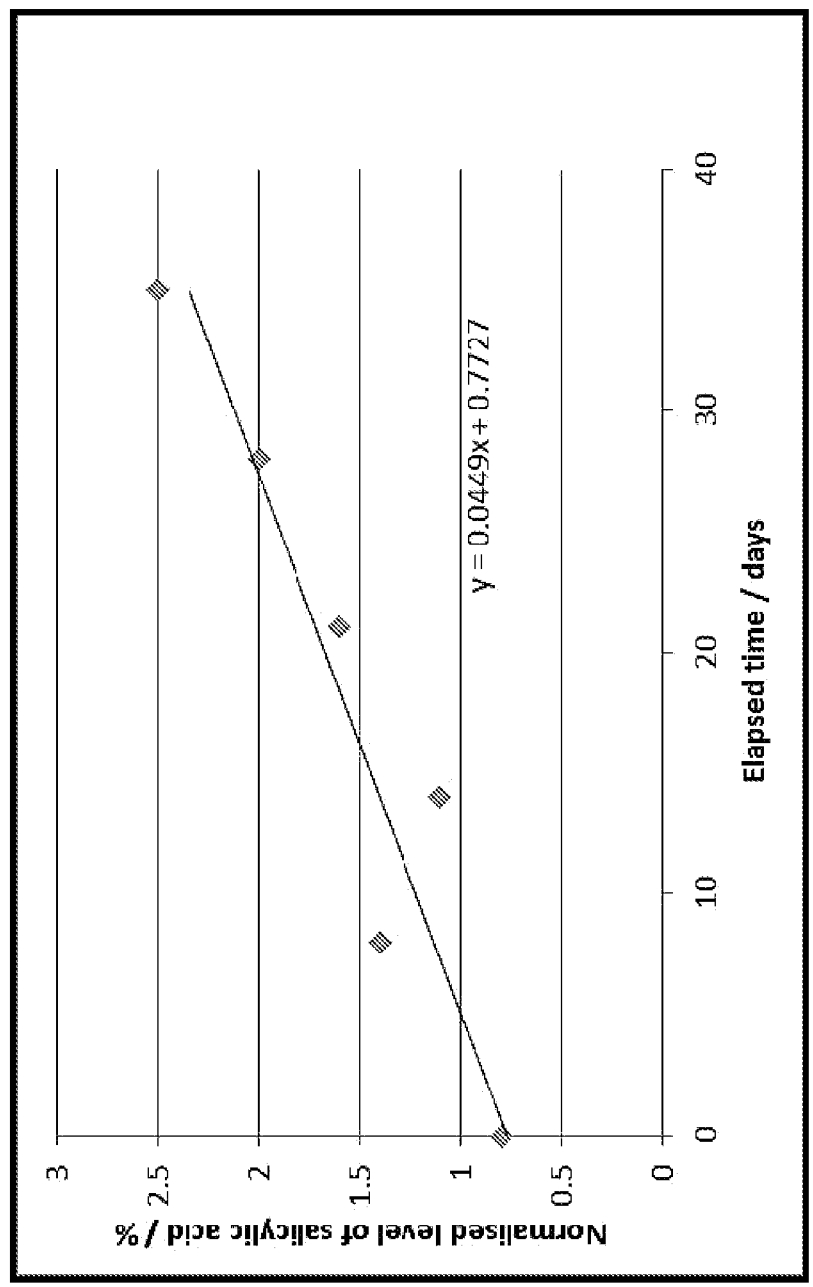
FIG. 2 is a plot of the normalized % of salicylic acid present in a test composition against the number of days elapsed since preparation of the composition, for a composition of 89 wt % glycerol+20EO, 10 wt % aspirin and 1 wt % saccharin. The test was conducted at 25° C.

The results are shown in Table 4 below, and in FIG. 2.

TABLE 4

| Day | Normalised % salicylic acid |
| --- | --- |
| 0 | 0.8 |
| 8 | 1.4 |
| 14 | 1.1 |
| 21 | 1.6 |
| 28 | 2.0 |
| 35 | 2.5 |

The average degradation rate is 0.0714%/day. Extrapolation from these results gives a predicted shelf life of 205 days.

The results of the above Examples and Comparative Examples are summarised in Table 5 below:

TABLE 5

| | Aspirin (wt %) | Glycerin Triacetate (wt %) | Glycerol + 20EO (wt %) | Saccharin (wt %) | Spearmint Oil (wt %) | Degradation rate (wt %/day) | Predicted shelf-life (days) |
| --- | --- | --- | --- | --- | --- | --- | --- |
| Ex. 2 | 2.5 | 96.5 | — | 1.0 | — | 0.025 | 400 |
| Ex. 3 | 2.5 | 96.35 | — | 1.0 | 0.15 | 0.023 | 435 |
| Ex. 4 | 2.5 | 96.5 | — | 1.0 | — | 0.0288 | 360 |
| Comp. Ex. 1 | 10 | — | 90 | — | — | 0.102 | 124 |
| Comp. Ex. 2 | 10 | — | 89 | 1.0 | — | 0.0714 | 205 |

It can be seen that the degradation rate of aspirin and thereby the shelf-life of the liquid composition is improved dramatically for compositions according to the invention. Shelf life of a year or longer is possible. A comparison of Comparative Examples 1 and 2 shows that the presence of saccharin provides a significant increase in stability. Furthermore, a comparison of Comparative Example 2 with Examples 2-4 reveals a dramatic improvement in stability when the composition includes glycerin triacetate.

The above examples illustrate the improved properties of a composition according to the present invention.

Example 6—an In Vitro Study to Investigate the Anti-Tumour Effects of Liquid Aspirin in Adult Glioblastoma, Paediatric High Grade Glioma and Medulloblastoma Introduction Soluble aspirins currently on the market are in fact dispersible and therefore still contain grains that sit on the gastric mucosa causing gastric side effects. The categorization as "soluble" is therefore not accurate. Alternative aspirin products are powders that quickly disperse in water. No truly shelf stable liquid formulation of acetylsalicylic acid (ASA) has been successfully produced, until now. The unique liquid ASA described herein (referred to in this Example as 'liquid aspirin') is expected to show a significant reduction in gastrointestinal side effects.

As described herein, liquid aspirin contains ASA and two excipients: glycerin triacetate (triacetin) and saccharin (Sac). All three ingredients are pharmaceutically approved and have been shown to have compelling anti-tumour properties.

Triacetin has been shown to significantly augment drug delivery across the blood brain barrier (BBB), suggesting that this combination could be highly effective against glioblastoma (GBM) [Van Tellingen et al., Overcoming the blood-brain tumor barrier for effective glioblastoma treatment. *Drug Resist. Updat.* 19, 1-12 (2015)].

Saccharin based compounds have been proposed as a new class of anti-cancer agent (Mahon et al., Saccharin: a lead compound for structure-based drug design of carbonic anhydrase IX inhibitors. Bioorg Med Chem 2015 Feb. 15; 23(4):849-54, incorporated herein by reference). Proescholdt et al. ('Function of carbonic anhydrase IX in glioblastoma multiforme', Neuro Oncol, 2012, Vol. 14, pp. 1357-1366) suggest that inhibition of carbonic anhydrase IX is a potential metabolic target for the treatment of glioblastoma patients.

Of the three components, aspirin has demonstrated the most potent anti-tumour effect, particularly against GBM. An initial in vivo study highlighted that the administration of aspirin into an established Fischer 344 rat glioma model (Aas, A. T., Brun, A., Blennow, C., Stromblad, S., & Salford, L. G. The RG2 rat glioma model. *J. Neurooncol.* 23, 175-183 (1995)) significantly inhibited the growth of differentiated malignant glioblastoma RG2 cells both when administered the day before tumour cell inoculation as well as in established rat glioblastoma tumours (Aas, A. T., Tonnessen, T. I., Brun, A., & Salford, L. G. Growth inhibition of rat glioma cells in vitro and in vivo by aspirin. *J. Neurooncol.* 24, 171-180 (1995)).

Prostaglandin E2 (PGE2) has been shown to have an important role in both immunosuppression and tumour growth. As a PGE2 inhibitor, aspirin has been shown to reduce in vitro tumour cell proliferation. Aspirin dosage studies were conducted, evaluating the effect of both high and low dose aspirin exposure on PGE2 synthesis in the in vitro C6 glioma model. These studies revealed that aspirin directly inhibited PGE2 synthesis in C6 cells and that critically, low-dose aspirin is as effective as high-dose aspirin in mediating this response (Hwang, S. L. et al. Effect of aspirin and indomethacin on prostaglandin E2 synthesis in C6 glioma cells. *Kaohsiung. J. Med. Sci.* 20, 1-5 (2004)).

Human A172 glioblastoma cells treated with aspirin induced significant apoptosis (programmed cell death) [Kim, S. R. et al. Aspirin induces apoptosis through the blockade of IL-6-STAT3 signaling pathway in human glioblastoma A172 cells. *Biochem. Biophys. Res. Commun.* 387, 342-347 (2009)]. The underlying mechanism for this response was a reduction in the level of phosphorylated signal transducer and activator of transcription 3 (STAT3), specifically pTyr-STAT3. STAT3 is a transcription factor that is required for survival of A172 cells. This conclusion was supported by measuring cyclin D1, XIAP, and Bcl-2 transcription that was notably attenuated after aspirin treatment (Kim et al., supra). Implicating STAT3 further, the expression and secretion of interleukin-6 (IL-6) (that induces STAT3 phosphorylation), was notably inhibited by aspirin treatment (Kim et al., supra).

Drawing from these findings, it is known that hypoxia can activate STAT3 and subsequently induce angiogenesis (the development of blood vessels) [Greten, F. R. & Karin, M. Peering into the aftermath: JAKi rips STAT3 in cancer. *Nat. Med.* 16, 1085-1087 (2010)]. In most solid malignancies, persistent STAT3 signalling is triggered by an autocrine-paracrine production of IL-6 that is noticeably higher in a hypoxic environment (Song, Y. Y. et al. STAT3, p-STAT3 and HIF-1alpha are associated with vasculogenic mimicry and impact on survival in gastric adenocarcinoma. *Oncol. Lett.* 8, 431-437 (2014)). Hypoxia is a hallmark of GBM, with tumours showing pseudopalisades of neoplastic cells surrounding areas of frank necrosis as well as signs of vascular proliferation. These areas of peri-necrotic hypercellularity have been well characterized and are not the result of increased proliferation. As one would predict, these regions have high levels of hypoxia-induced factor 1 alpha (HIF1α) expression, resulting in pro-angiogenic vascular endothelial growth factor (VEGF) secretion as well as elevated IL-6. This in turn drives vascular proliferation. However, the vessels that are generated in response to VEGF within this environment are severely malformed (Jain, R. K. Normalizing tumor microenvironment to treat cancer: bench to bedside to biomarkers. *J. Clin. Oncol.* 31, 2205-2218 (2013)). The result is deregulated vessel structure with gaps between endothelial cells and an absence of pericytes. Due to this malformation and inherent leakiness, the interstitial pressure is increased resulting in vascular stasis with corresponding exacerbation of hypoxia and increased microvascular thrombosis (Jain et al., supra). Strikingly, it has been shown that aspirin selectively suppresses inflammation, and specifically IL-6-induced T-helper cell 17. This mediates the down regulation of acetyl-STAT3 expression as well as blocking IL-17A-induced inflammation and IL-6 production. This reduction of IL-6 production will then result in a concomitant reduction in active (phosphorylated) STAT3.

More recently, it has been shown that aspirin represses the transcriptional activity of the β-catenin/TCF protein complex. As a consequence of this, aspirin directly inhibits GBM proliferation and invasion as well as inducing apoptosis (Jin, T., George, F., I, & Sun, J. Wnt and beyond Wnt: multiple mechanisms control the transcriptional property of beta-catenin. *Cell Signal.* 20, 1697-1704 (2008)). The results presented within this study suggest that aspirin exerts its anti-neoplastic action by suppressing the β-catenin/TCF signalling pathway in GBM. This is particularly striking as recent data has highlighted that FoxM1 promotes the development and progression of GBM by regulating key factors involved in cell division, epithelial to mesenchymal transition (EMT), invasion, angiogenesis and upregulation of the Wnt/β-catenin signalling network (Wang, Z., Zhang, S., Siu, T. L., & Huang, S. Glioblastoma multiforme formation and EMT: role of FoxM1 transcription factor. *Curr. Pharm. Des* 21, 1268-1271 (2015)). A deregulated Wnt/β-catenin network has been reported in GBM and it has been suggested that this could also constitute a therapeutic target (Zhang, K. et al. ICAT inhibits glioblastoma cell proliferation by suppressing Wnt/beta-catenin activity. *Cancer Lett.* 357, 404-411 (2015)).

Experimental Method and Results

Many of the established glioma cell lines, such as C6, A172, U87, U373 and U251 have been grown/passaged in research laboratories around the world for many years and, as a consequence, display a high degree of cellular heterogeneity rendering them increasingly dissimilar to their original primary/early passage cultures and, indeed, from the biopsy from which they were derived.

To address this issue, we used a panel of patient-derived (adult and paediatric) ex vivo GBM low passage cell cultures, which have been characterized at the molecular level, including DNA fingerprinting (Prof. G. Pilkington, Brain Tumour Research Centre, University of Portsmouth, UK). These cells are truly representative of the patient GBM and, as a result, any anti-tumour effect observed will have clinical relevance. This extensive cell culture bio-bank allows screening of novel anti-GBM therapeutics prior to in vivo studies and clinical trials.

It is also critical to compare these novel therapeutics against the currently prescribed frontline chemotherapeutics. Consequently, our studies also include temozolomide, which is a standard of care treatment for GBM.

Non-neoplastic astrocytes provide a control element within these studies. These are non-cancerous and any proposed therapeutic will preferably have selective anti-cancer action (i.e. not kill normal, non-tumor cells).

Viability studies were conducted to compare the effect of liquid aspirin (ASP), triacetin (ASP vehicle), and temozolomide (TMZ) in five adult GBM ex vivo cell lines from our panel. Results are shown in FIGS. 4A to 4E. Liquid aspirin showed notably better induction of cell death in all GBM cells tested.

Figure 6A:
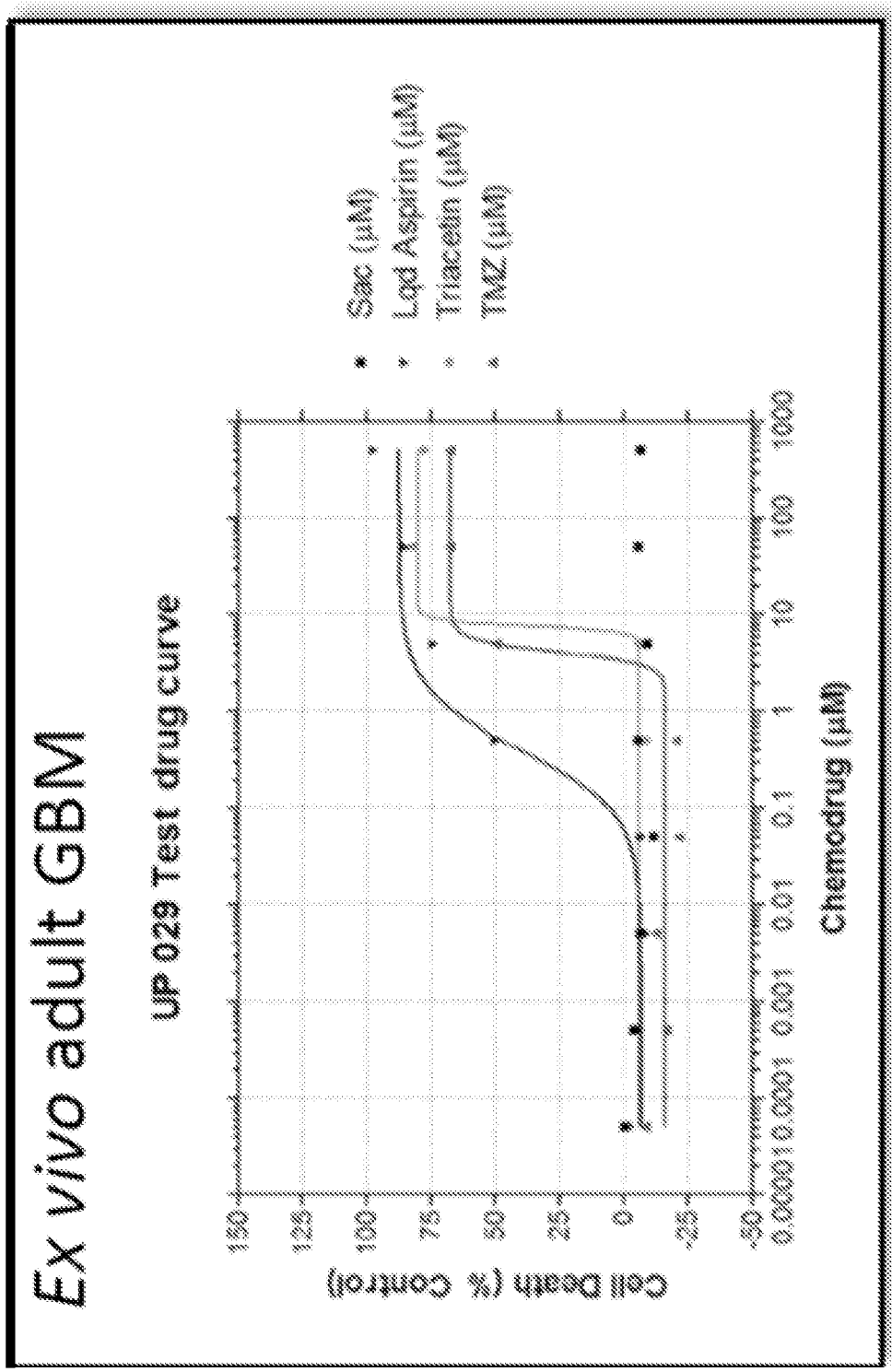
FIGS. 6A to 6C. (A) Chart showing percentage cell death in ex vivo biopsy-derived UP029 cells with varying concentration of drug (saccharin-only (Sac), liquid aspirin (Lqd Aspirin), triacetin-only, temozolomide-only (TMZ)). (B) and (C) Charts showing synergy analysis of ex vivo biopsy-derived UP029 cells following treatment with liquid aspirin, saccharin-only and triacetin-only. Synergy (of the liquid aspirin compound) was noted (in order to kill 30%, 50% and 70%) compared to each agent alone with the exception of triacetin-alone (at 90% reduced cell viability) at 96 hours post-treatment, where the highest dosages of triacetin alone was reducing overall cell viability.
Figure 6B:
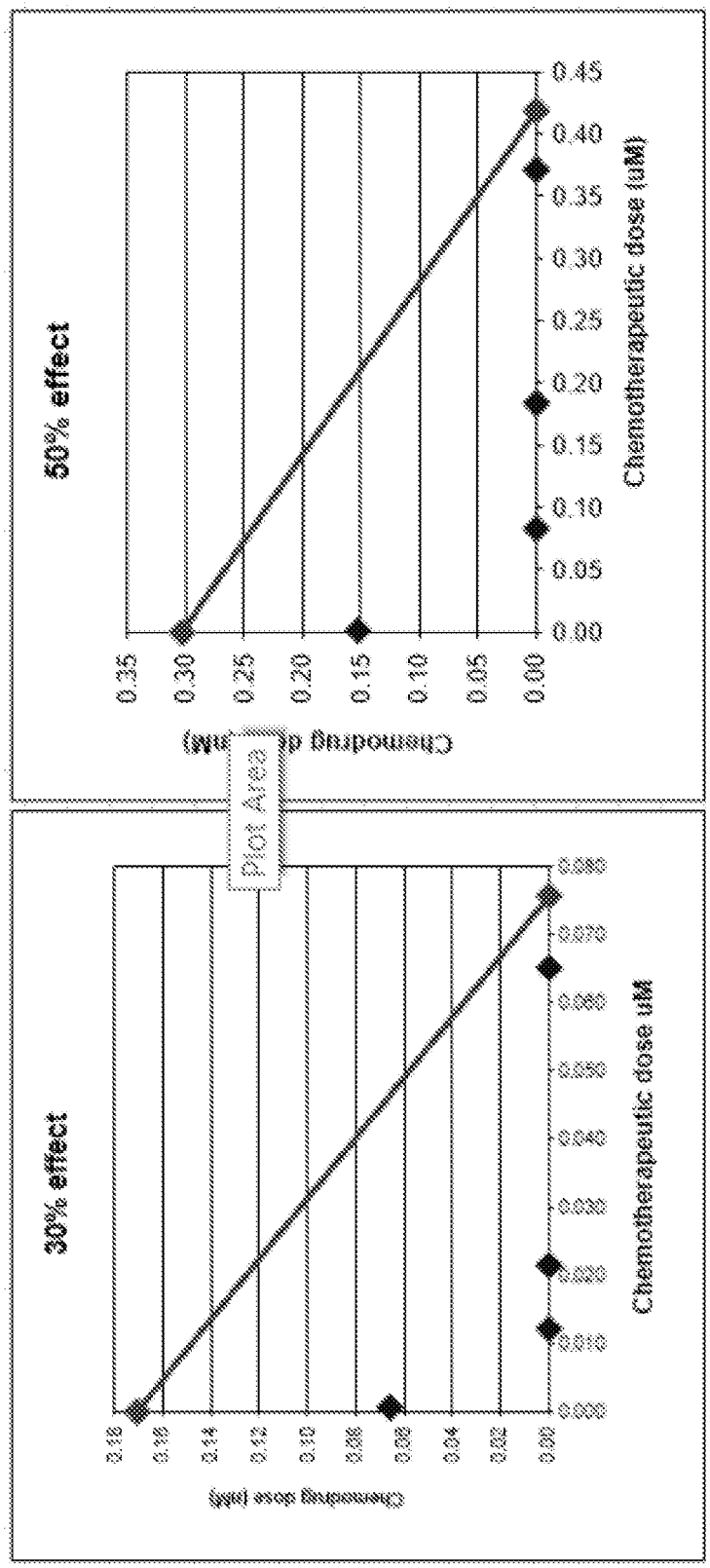
Figure 6C:
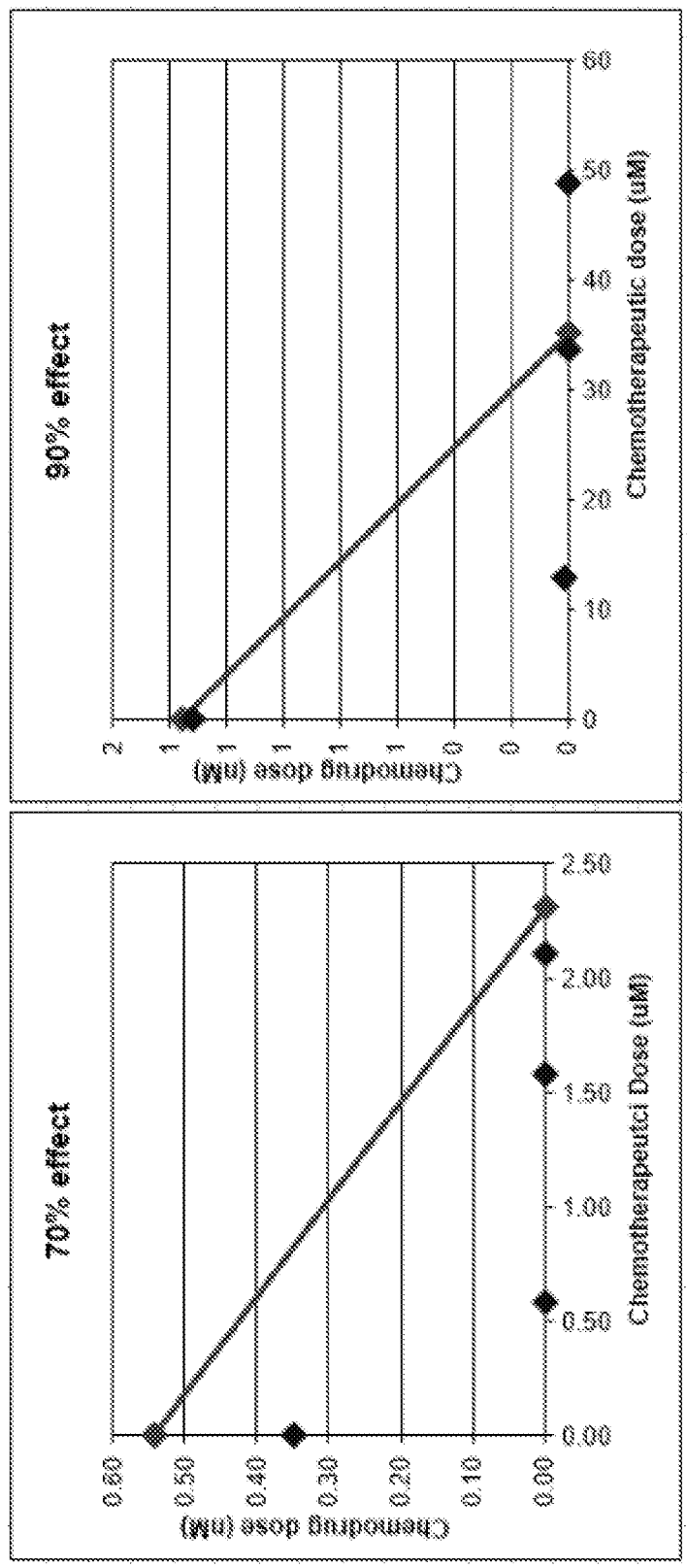

Synergy studies were also conducted to directly address the specific anti-tumour efficacy of each of aspirin, triacetin and saccharin (Sac) as individual components and the triple-formulation of aspirin, triacetin and saccharin (liquid aspirin). We have significant experience conducting this type of analysis and importantly can differentiate between additive effects versus a synergistic response (Hallden, G. et al. Novel immunocompetent murine tumor models for the assessment of replication-competent oncolytic adenovirus efficacy. *Mol. Ther.* 8, 412-424 (2003); Cheong, S. C. et al. E1A-expressing adenoviral E3B mutants act synergistically with chemotherapeutics in immunocompetent tumor models. *Cancer Gene Ther.* 15, 40-50 (2008)). FIGS. 6B and 6C show synergy of liquid aspirin in order to kill 30%, 50% and 70% of UP 029 cells compared to use of each agent alone with the exception of triacetin-alone at 90% reduced cell viability, where the highest dosages of triacetin alone reduced overall cell viability.

Figure 7A:
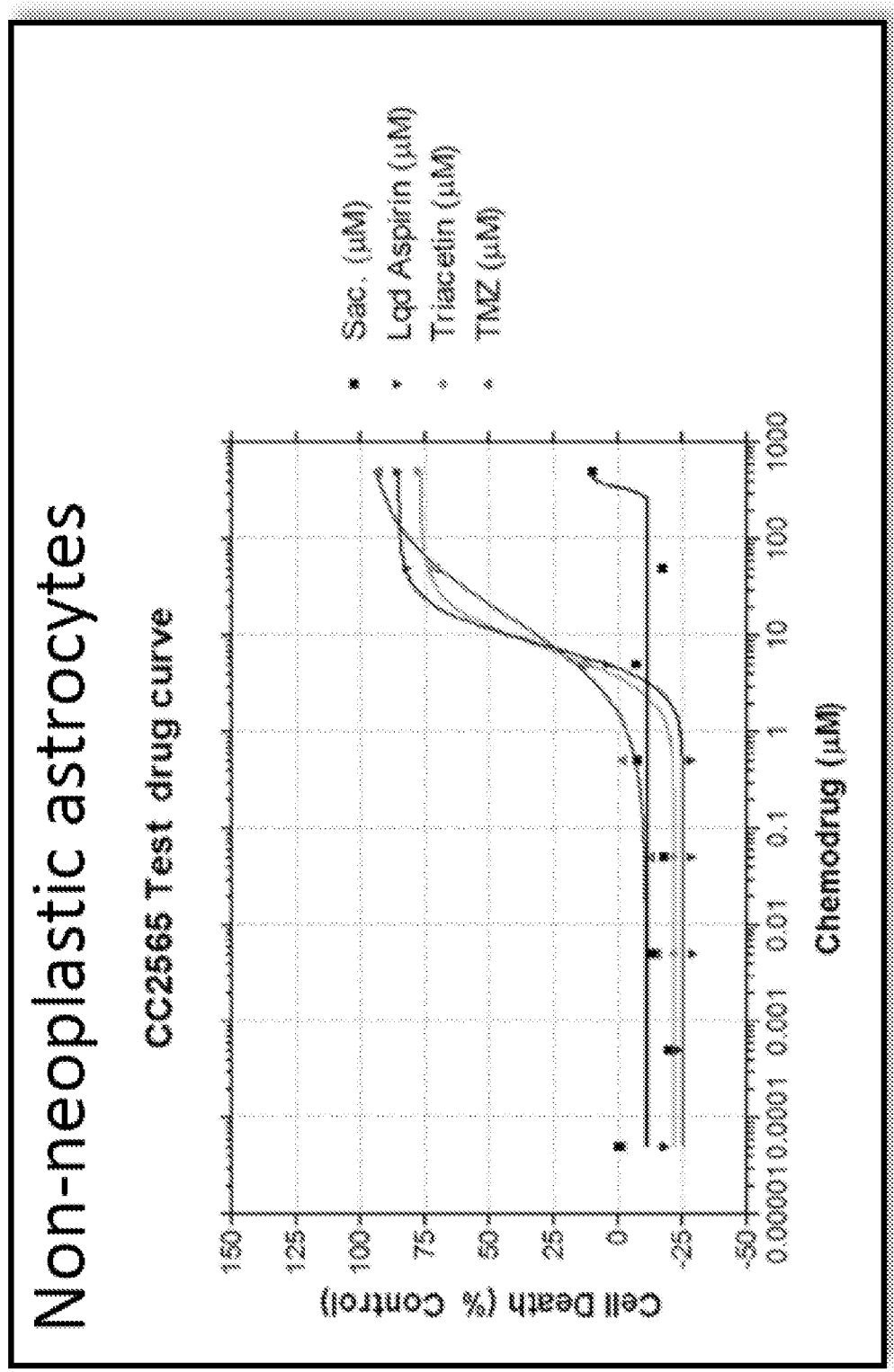
FIGS. 7(A) to 7(F). Charts showing percentage cell death (MTS viability analysis) of control and biopsy-derived cell lines 96 hours post-treatment with varying concentration of drug (saccharin-only (Sac), liquid aspirin-only (Lqd Aspirin), triacetin-only, or temozolomide-only (TMZ)). (A) Non-neoplastic astrocytes (CC2565) included as a control, (B) SEBTA 003 (C) SEBTA 023 (D) KNS42 (E) SNF188 (F) SEBTA 025. Each plot is representative of 3 studies conducted in triplicate.
Figure 7B:
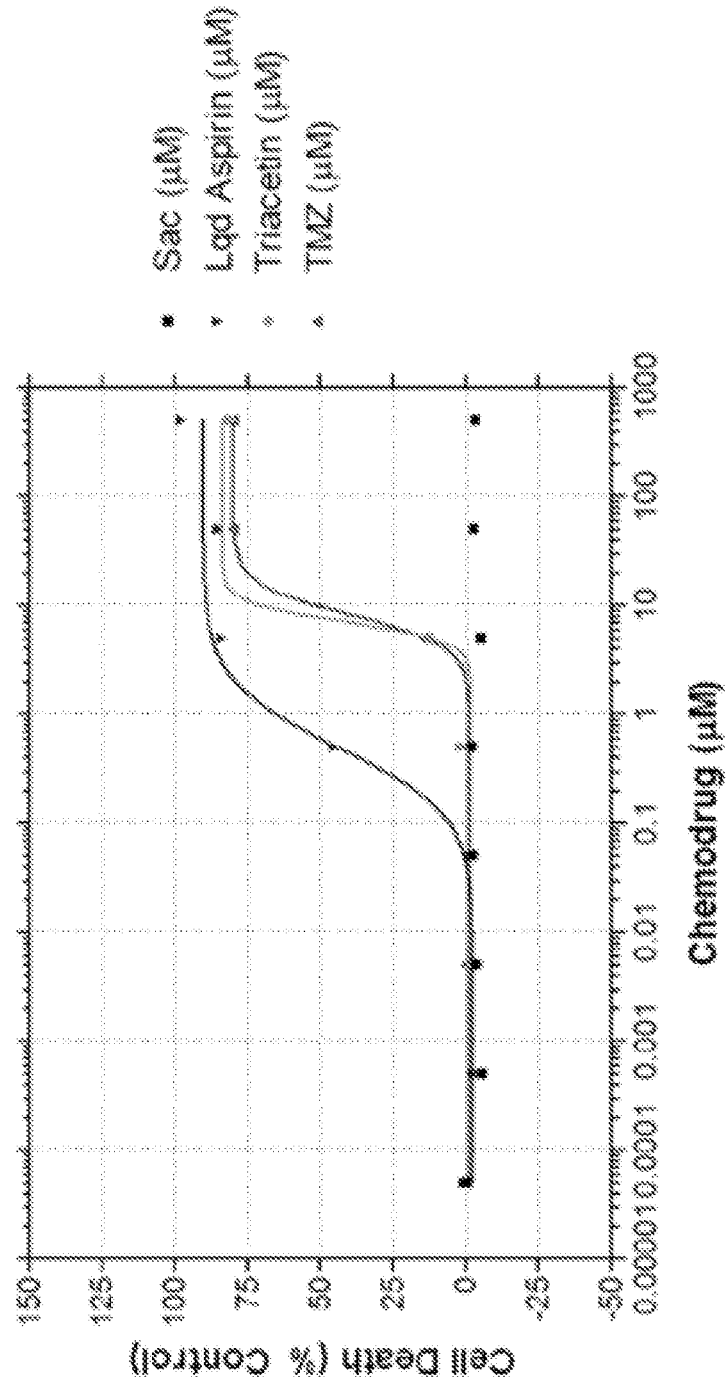
Figure 7C:
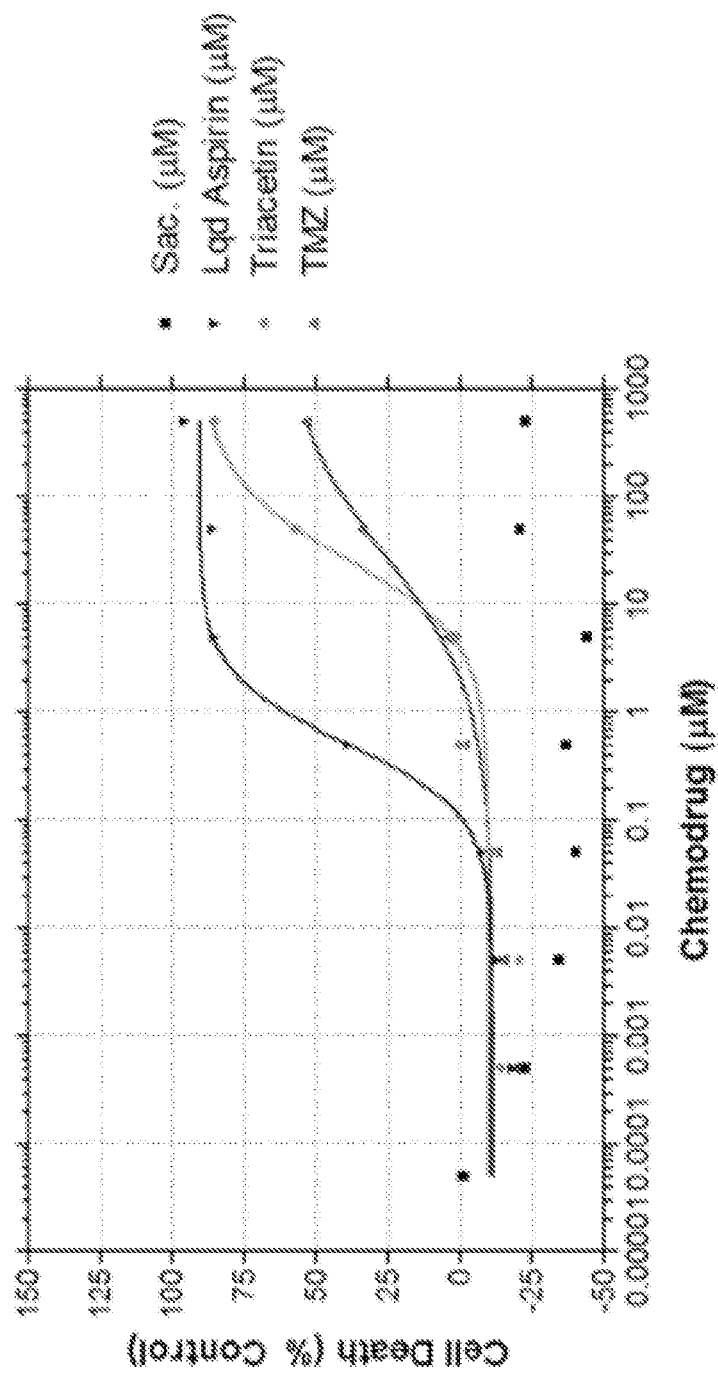
Figure 7D:
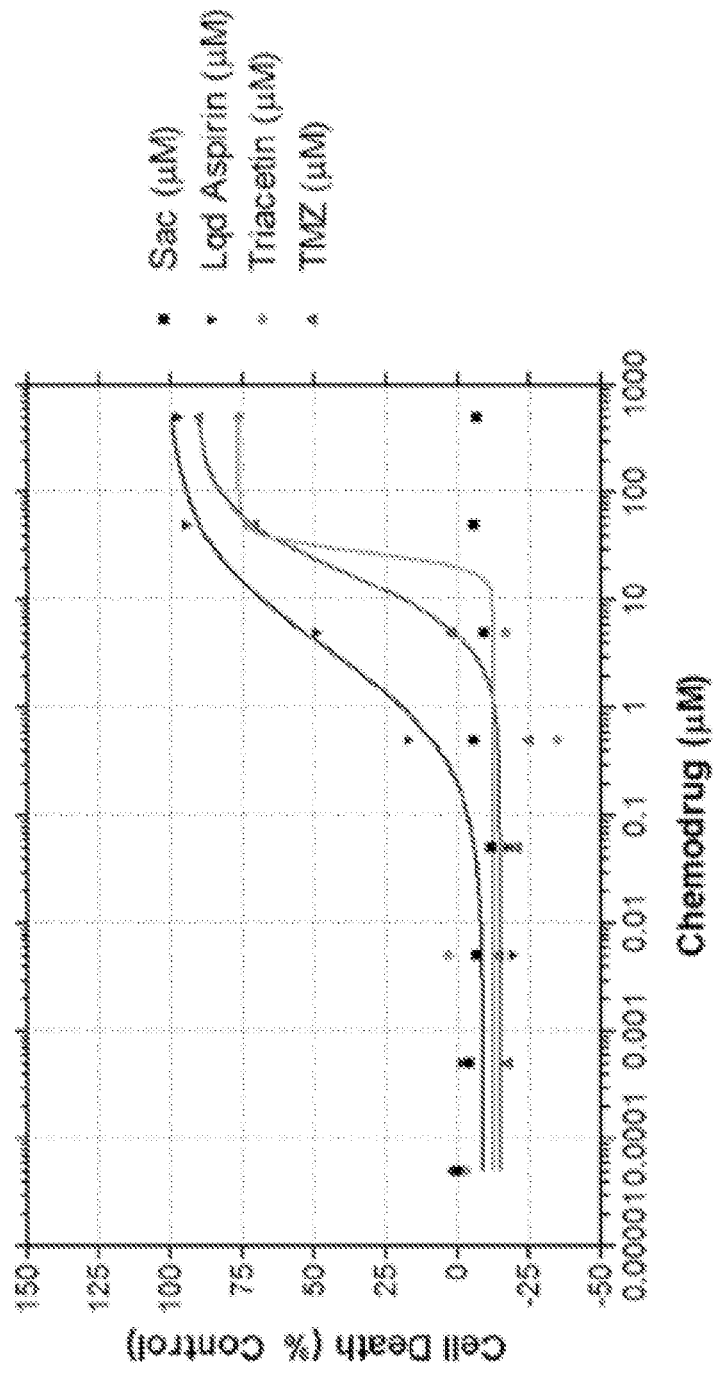
Figure 7E:
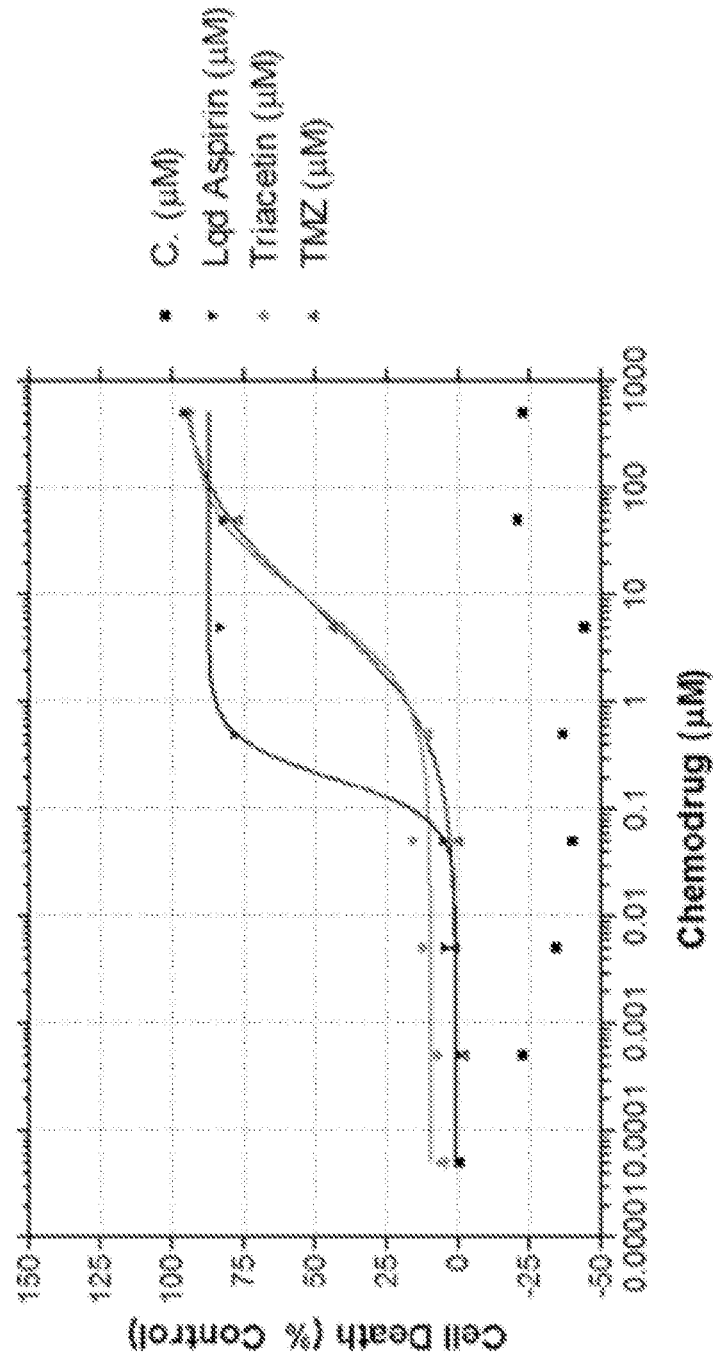
Figure 7F:
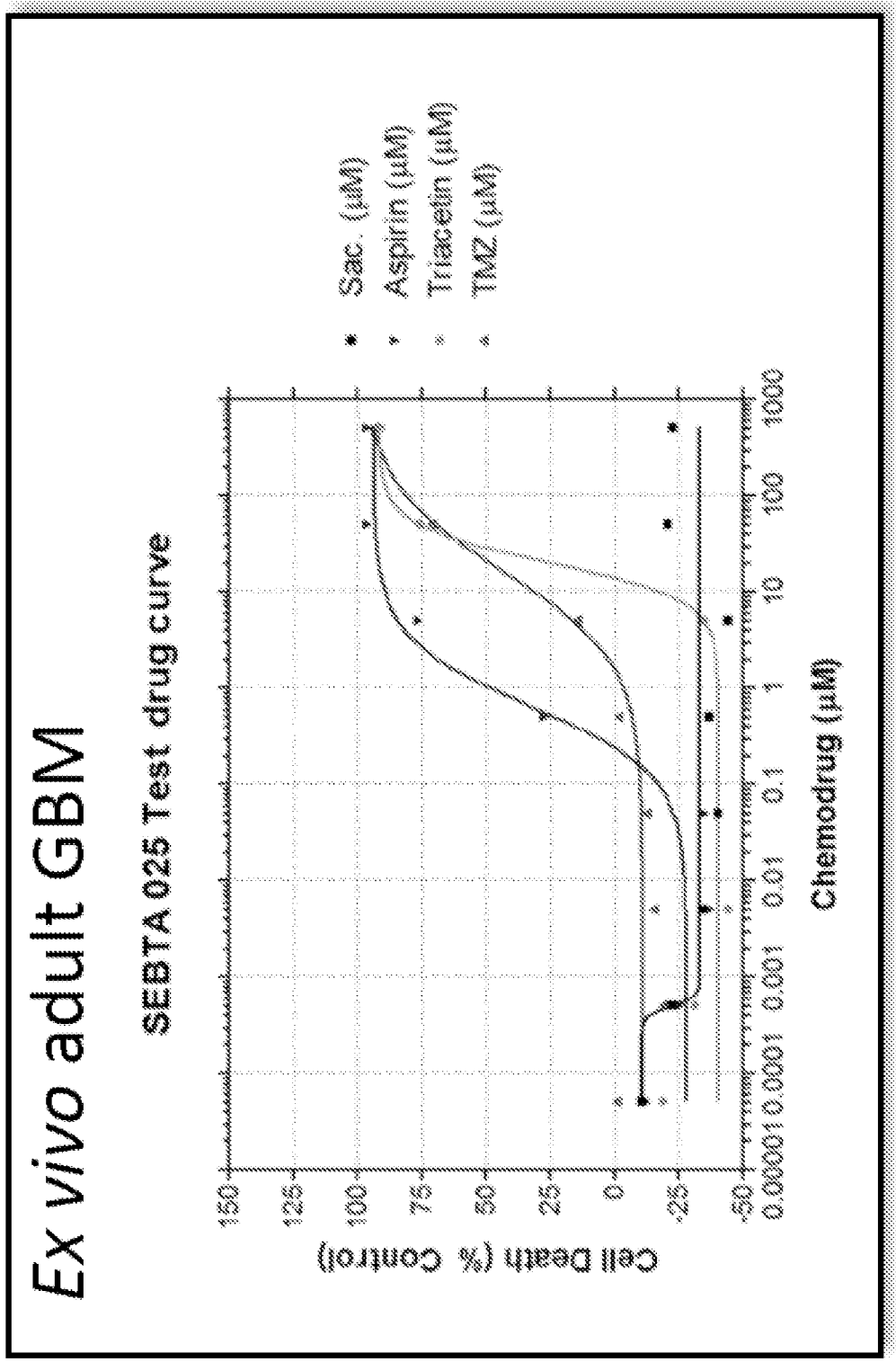

We also confirmed that liquid aspirin demonstrates anticancer specificity, i.e. is not toxic to non-neoplastic astrocytes. Results are shown in FIG. 7A to 7F which show liquid aspirin to have markedly better cell killing ability than triacetin or temozolomide; liquid aspirin typically having at least one order of magnitude greater potency in inducing cell death than triacetin or temozolomide. Liquid aspirin had significantly less toxicity when added to non-neoplastic cells (FIG. 7A). Indeed, the associated toxicity noted within the astrocyte cell line could be associated with triacetin-alone (which demonstrated a similar MTS-viability profile).

REFERENCES

The following are incorporated herein by reference:
1. Lan et al. "Antitumor effect of aspirin in glioblastoma cells by modulation of β-catenin/T-cell factor-mediated transcriptional activity", J Neurosurg, 2011, Vol. 115, pp. 780-788;
2. M. W. Brown, 'Characterisation Of The Effects Of Chronic Aspirin Treatment On The Viability And Proliferation Of Stage 4 Glioblastoma Cells', *Diffusion: the UCLan Journal of Undergraduate Research*, Vol. 6, Issue 2, December 2013;
3. Aas et al., 'Growth inhibition of rat glioma cells in vitro and in vivo by aspirin', *Journal of Neuro-Oncology*, 1995, Vol. 24, Issue 2, pp. 171-180;
4. Ning et al., 'Overexpression of S100A9 in human glioma and in-vitro inhibition by aspirin', *European Journal of Cancer Prevention*, 2013, Vol. 22, Issue 6, pp. 585-595;
5. Hwang et al., 'Effect of aspirin and indomethacin on prostaglandin E2 synthesis in C6 glioma cells', *Kaohsiung J Med Sci*, 2004, Vol. 20, pp. 1-5;
6. Okada et al., 'Integration of epidemiology, immunobiology, and translational research for brain tumors', *Ann N Y Acad Sci*, 2013, Vol. 1284, pp. 17-23;
7. Rothwell et al., 'Effect of daily aspirin on long-term risk of death due to cancer: analysis of individual patient data from randomised trials', Lancet, 2011, Vol. 377, pp. 31-41;
8. K. D. Rainsford, *'Aspirin and Related Drugs'*, 2004 (book);
9. Douthwaite and Lintott, 'Gastroscopic observations of the gastric mucosa after use of aspirin', *Lancet*, 1938, Vol. 232, pp. 1222-1225;
10. Hurst and Lintott, 'Aspirin as a cause of hematemesis', *Guy's Hosp Rep*, 1939, p. 173;
11. D. J. Levy 'An aspirin tablet and gastric ulcer', *N Engl J Med*, 2000, Vol. 343, No. 12, p. 863 (photograph);
12. Rainsford et al. 'Electronmicroscopic observations on the effects of orally administered aspirin and aspirin-bicarbonate mixtures on the development of gastric mucosal damage in the rat', *Gut*, 1975, Vol. 16(7), pp. 514-527;
13. Jaiswal et al. IUPHAR 9th Int. Conference of Pharmacology, 1984;
14. Liversage et al. 'Drug particle size reduction for decreasing gastric irritation and enhanced absorption of Naproxen in rats', *Int J Pharm*, 1995, Vol. 125(2), pp. 309-313;
15. Gyory et al. 'Effect of particle size on aspirin-induced gastrointestinal bleeding', *Lancet, Vol.* 292, No. 7563, pp. 300-302;
16. M. I. Grossman et al. 'Fecal Blood Loss Produced By Oral And Intravenous Administration Of Various Salicylates', *Gastroenterology*, 1961, Vol. 40, pp. 383-388;
17. Kevin et al., 'Acute effect of systemic aspirin on gastric mucosa in man', *Digestive Diseases and Sciences*, 1980, Vol. 25, Issue 2, pp 97-99;
18. Cooke et al., 'Failure of intravenous aspirin to increase gastrointestinal blood loss', *British medical journal*, 1969; Vol. 3(5666), pp. 330-332;
19. Wallace et al., 'Adaptation of rat gastric mucosa to aspirin requires mucosal contact' *Am J Physiol*, 1995, Vol. 268, G134-8;
20. Cryer et al. 'Effects of low dose daily aspirin therapy on gastric, duodenal and rectal prostaglandin levels and on mucosal injury in healthy humans', *Gastroenterology*, 1999, Vol. 117, pp. 17-25;
21. Lichtenberger et al., 'Where is the evidence that cyclooxygenase inhibition is the primary cause of non-steroidal anti-inflammatory drug (NSAID)-induced gastrointestinal injury? Topical injury revisited', *Biochemical Pharmacology*, 2001, Vol. 61, pp. 631-637;
22. Ligumsky M et al., 'Aspirin can inhibit gastric mucosal cyclo-oxygenase without causing lesions in the rat', *Gastroenterology*, 1983, Vol. 84, pp 756-61;
23. Zhao et al., 'Clinical Research Feasibility of intravenous administration of aspirin in acute coronary syndrome', *Journal of Geriatric Cardiology*, 2008, Vol. 5 No. 4, pp. 212-216;
24. Mashita et al., 'Oral but not parenteral aspirin upregulates COX-2 expression in rat stomachs: a relationship between COX-2 expression and PG deficiency', *Digestion*, 2006, Vol. 73(2-3), pp. 124-32;
25. Hall, S L; Lorenc, T (1 Feb. 2010). "Secondary prevention of coronary artery disease". *American family physician* 81 (3): 289-96;
26. Fengming Lan et al., Antitumor effect of aspirin in glioblastoma cells by modulation of β-catenin/T-cell factor-mediated transcriptional activity. J Neurosurg 115: 780-788, 2011;
27. Morris et al., Effects of Low-Dose Aspirin on Acute Inflammatory Responses in Humans. The Journal of Immunology. 2009; 183:2089-2096;
28. Gasic G I, et al. Lancet. 1972; 2:932-937;
29. Tsen et al., Triacetin-based acetate supplementation as a chemotherapeutic adjuvant therapy in glioma. Int J Cancer. 2014 Mar. 15; 134(6):1300-1310;
30. Long et al., 'Acetate Supplementation Induces Growth Arrest of NG2/PDGFRa-Positive Oligodendroglioma-Derived Tumor-Initiating Cells', PLoS One, 2013, e80714;
31. Mahon et al., Saccharin: a lead compound for structure-based drug design of carbonic anhydrase IX inhibitors. Bioorg Med Chem 2015 Feb. 15; 23(4):849-54;
32. Proescholdt et al. ('Function of carbonic anhydrase IX in glioblastoma multiforme', Neuro Oncol, 2012, Vol. 14, pp. 1357-1366;
33. Buck M L et al., 'Use of Aspirin in children with cardiac disease', Pediatr Pharm, 2007, Vol. 13(1);
34. Garcia Albeniz. X et al., 'Aspirin for the prevention of colorectal cancer', Best Pract Res Clin Gastroenterol, 2011 August, Vol. 25(0), pp. 461-472.

The invention claimed is:

1. A liquid composition comprising a solution of aspirin, glycerin triacetate, and saccharin,
wherein the composition comprises 0.5 to 7 wt % of the aspirin and 90 to 99 wt % of the glycerin triacetate.

2. The composition according to claim 1, wherein the composition comprises 1 to 5 wt % of the aspirin.

3. The composition according to claim 1, wherein the composition comprises 0.5 to 3 wt % of the aspirin.

4. The composition according to claim 1, wherein the composition comprises 94 to 99 wt % of the glycerin triacetate.

5. The composition according to claim 1, wherein the composition comprises 95 to 97.5 wt % of the glycerin triacetate.

6. The composition according to claim 1, wherein the composition comprises 0.5 to 3 wt % of the aspirin and 94 to 99 wt % of the glycerin triacetate.

7. The composition according to claim 1, wherein the composition further comprises 0.1 to 3 wt % saccharin.

8. The composition according to claim 1, wherein the composition comprises 0 to 0.5 wt % water.

9. The composition according to claim 1, further comprising a flavoring agent.

10. The composition according to claim 9, wherein the flavoring agent is mint oil.

11. The composition according to claim 1, which is free of particulates.

12. The composition according to claim 1, which is designed for oral administration.

13. The composition according to claim 1, which is formulated for intravenous or intra-arterial administration.

14. The composition according to claim 1, which is formulated for inhalation or insufflation administration.

15. A method of preparing a liquid composition according to claim 1, the method comprising admixing the aspirin, the glycerin triacetate, and the saccharin.

16. The method according to claim 15, further comprising admixing a flavoring agent.

17. A packaged article comprising the composition as defined in claim 1, which is sealed therein.

18. The packaged article according to claim 17, which is selected from the group consisting of a bottle, pipette, syringe, vial, sachet, stick shot, and liquid gel capsule.

* * * * *